US010426495B2

United States Patent
Bonin, Jr. et al.

(10) Patent No.: US 10,426,495 B2
(45) Date of Patent: Oct. 1, 2019

(54) METHODS AND DEVICES FOR INSTALLING STANDARD AND REVERSE SHOULDER IMPLANTS

(71) Applicant: Smith & Nephew, Inc., Memphis, TN (US)

(72) Inventors: Henry Keith Bonin, Jr., Memphis, TN (US); David L Brumfield, Collierville, TN (US); Raymond H. Roberson, Jr., Eads, TN (US)

(73) Assignee: Smith & Nephew, Inc., Memphis, TN (US)

( * ) Notice: Subject to any disclaimer, the term of this patent is extended or adjusted under 35 U.S.C. 154(b) by 862 days.

(21) Appl. No.: 14/993,517

(22) Filed: Jan. 12, 2016

(65) Prior Publication Data

US 2016/0120555 A1    May 5, 2016

Related U.S. Application Data

(63) Continuation of application No. 13/814,124, filed as application No. PCT/US2011/043719 on Jul. 12, 2011, now Pat. No. 9,232,955.

(Continued)

(51) Int. Cl.
*A61B 17/17* (2006.01)
*A61B 17/15* (2006.01)
(Continued)

(52) U.S. Cl.
CPC .......... *A61B 17/1778* (2016.11); *A61B 17/15* (2013.01); *A61B 17/1764* (2013.01);
(Continued)

(58) Field of Classification Search
CPC .................................................. A61B 17/1778
See application file for complete search history.

(56) References Cited

U.S. PATENT DOCUMENTS 5,779,710 A    7/1998  Matsen, III
7,981,158 B2   7/2011  Fitz et al.
(Continued)

FOREIGN PATENT DOCUMENTS

WO    2010017307 A1    2/2010
WO    2010150223 A1   12/2010

OTHER PUBLICATIONS

International Search Report; Korean Intellectual Property Office; dated Mar. 23, 2012; 5 pages.

(Continued)

*Primary Examiner* — Andrew Yang
(74) *Attorney, Agent, or Firm* — Pepper Hamilton LLP

(57) ABSTRACT

Surgical procedures, tools and implants are disclosed for both conventional and reverse shoulder implant surgeries. The improved procedures, tools and implants relate to humeral head resurfacing, humeral head resection for standard implants, humeral head resection for reverse shoulder implants, glenoid resurfacing for standard shoulder implants and glenoid resurfacing for reverse shoulder implants. 3D scans and x-rays are used to develop virtual models of the patient anatomy, identify patient specific landmarks for anchoring guide wire installation blocks, templates and drill guides. 3D scans are also used to design patient specific tools and implants for the shoulder implant procedures and to pre-operatively determine the appropriate inclination and retroversion angles.

12 Claims, 14 Drawing Sheets

Related U.S. Application Data

(60) Provisional application No. 61/373,092, filed on Aug. 12, 2010.

(51) Int. Cl.
    *A61B 17/56*     (2006.01)
    *A61F 2/40*     (2006.01)
    *A61F 2/46*     (2006.01)

(52) U.S. Cl.
    CPC ........... *A61B 2017/568* (2013.01); *A61F 2/40* (2013.01); *A61F 2002/4085* (2013.01); *A61F 2002/4668* (2013.01); *Y10T 29/49* (2015.01)

(56) References Cited

U.S. PATENT DOCUMENTS

| | | |
|---|---|---|
| 8,066,708 B2 | 11/2011 | Lang et al. |
| 8,439,926 B2 | 5/2013 | Bojarski et al. |
| 8,858,561 B2 * | 10/2014 | White .................. A61B 17/175 606/86 R |
| 2007/0005074 A1 | 1/2007 | Chudik |
| 2009/0018546 A1 | 1/2009 | Daley |
| 2009/0254093 A1 | 10/2009 | White et al. |
| 2009/0318929 A1 | 12/2009 | Tornier et al. |
| 2010/0274253 A1 * | 10/2010 | Ure .................... A61B 17/1746 606/91 |

OTHER PUBLICATIONS

Written Opinion of the International Searching Authority; Korean Intellectual Property Office; dated Mar. 23, 2012; 7 pages.

\* cited by examiner

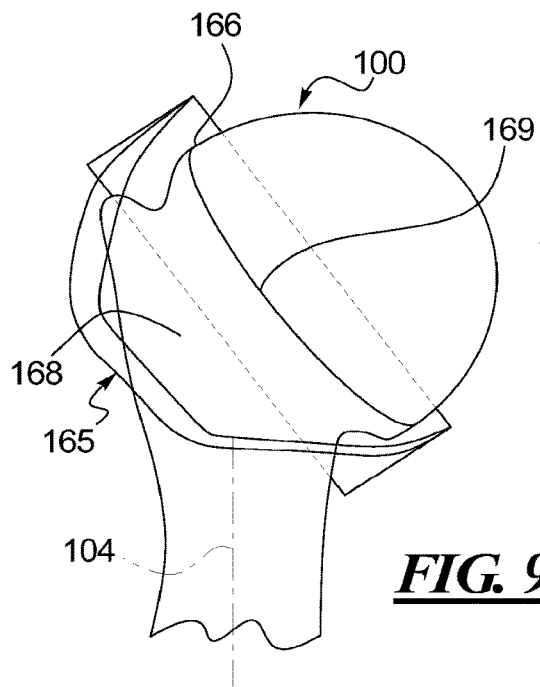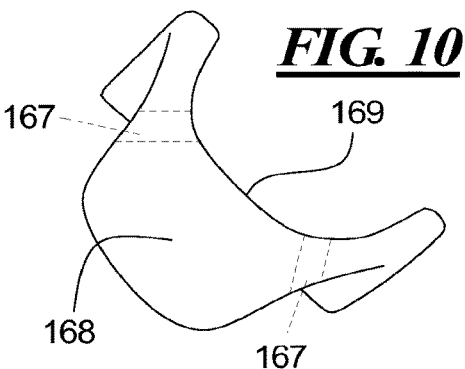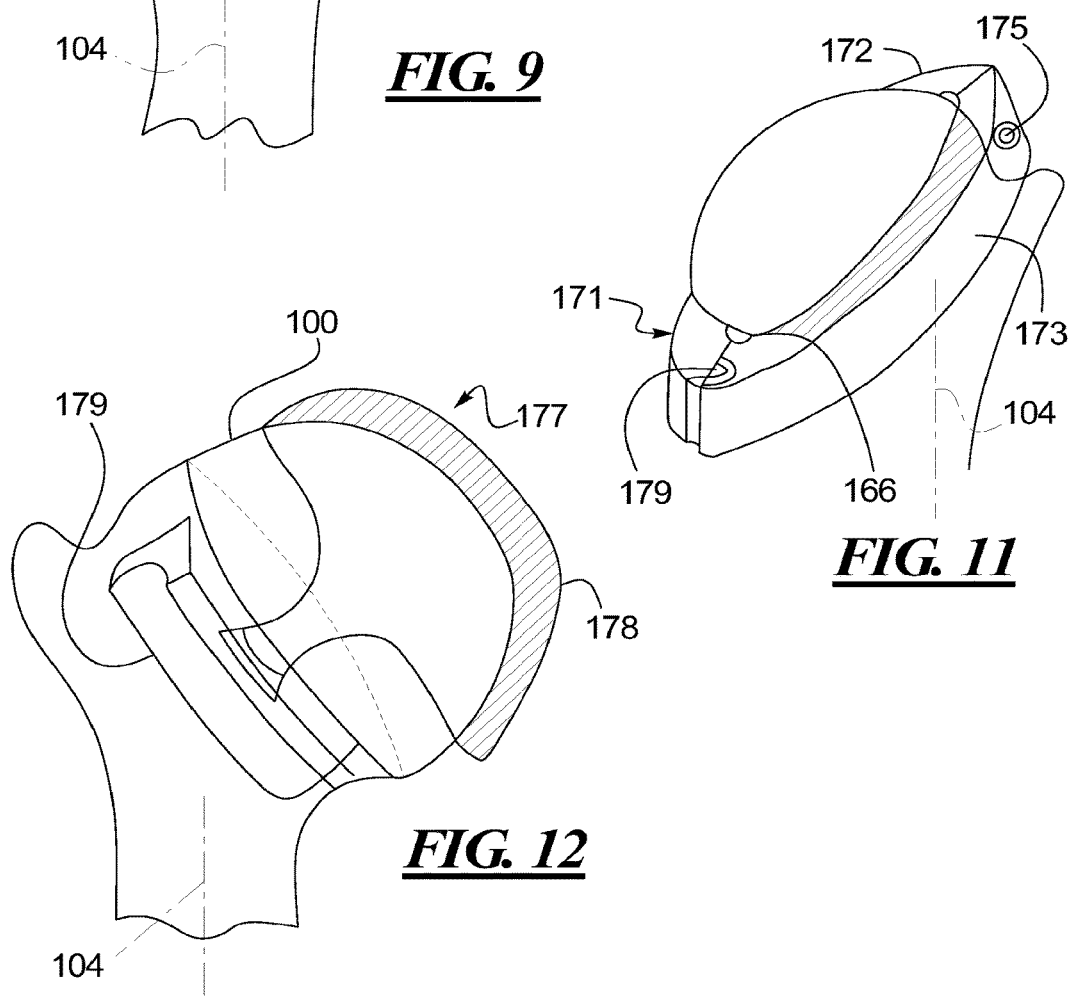
FIG. 9
FIG. 10
FIG. 11
FIG. 12

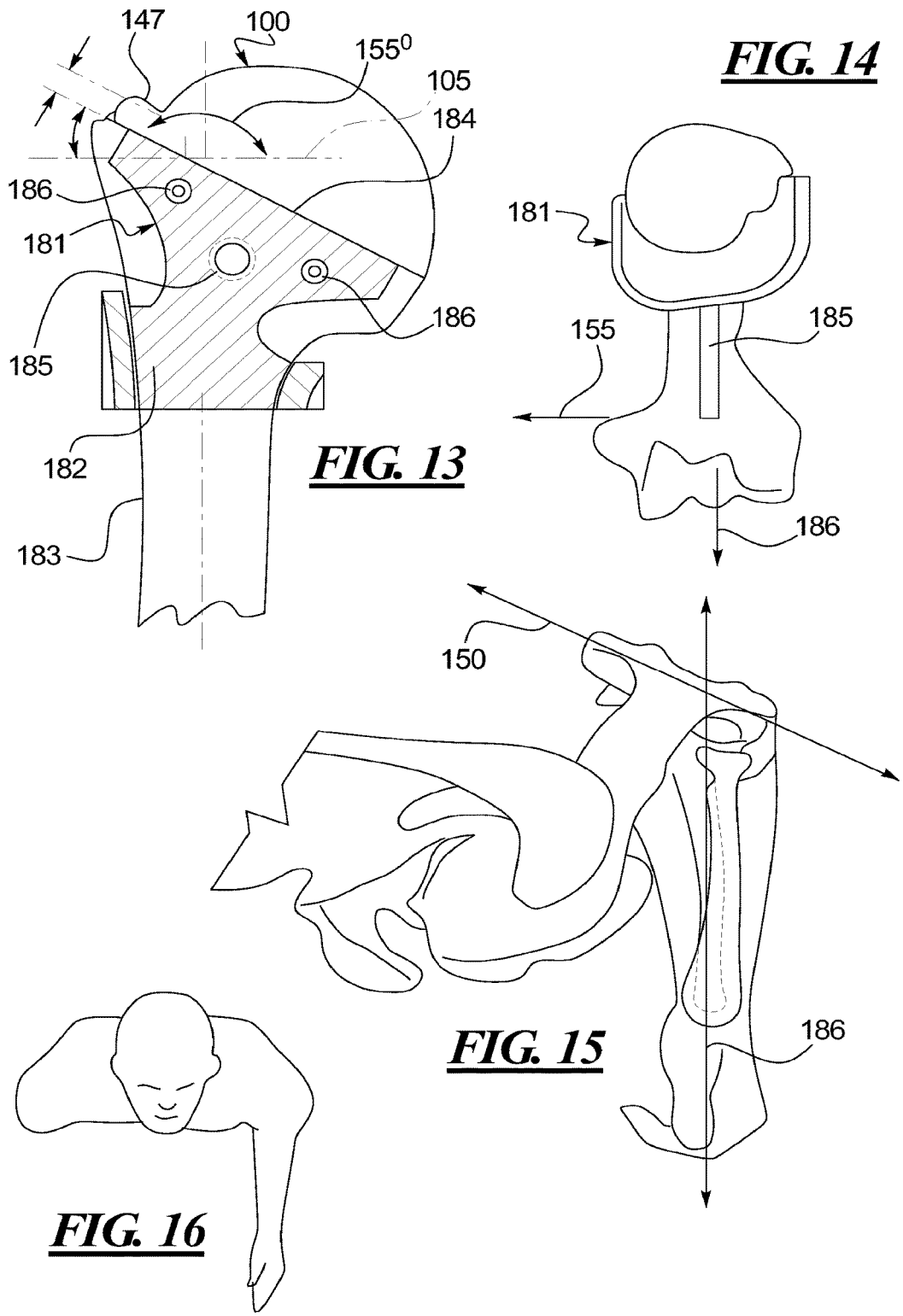

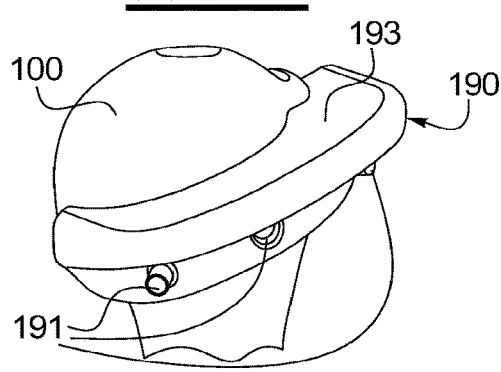
FIG. 17
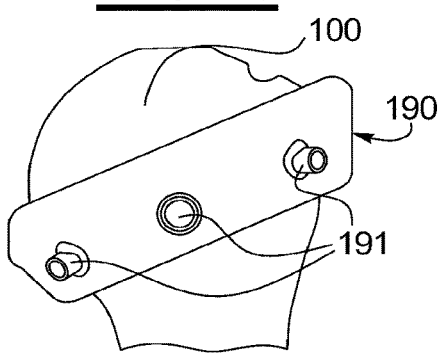
FIG. 18
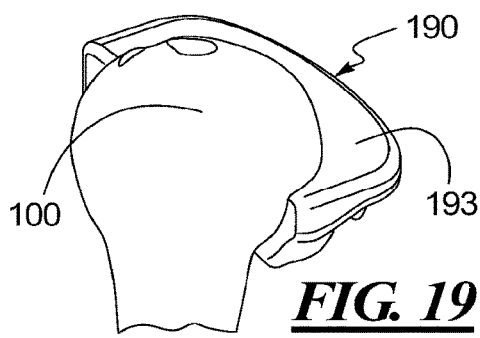
FIG. 19
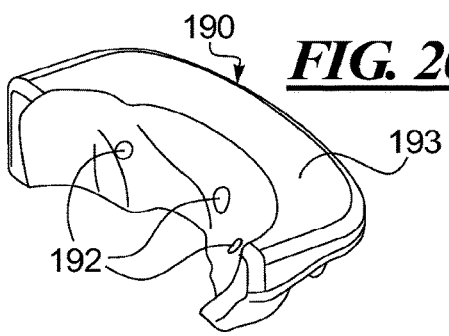
FIG. 20
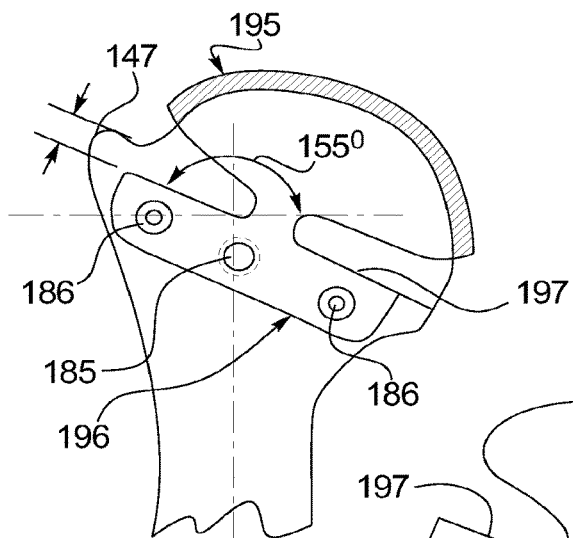
FIG. 21
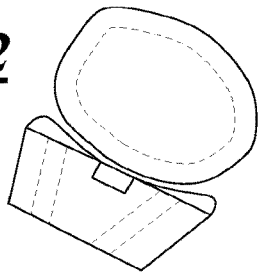
FIG. 22
FIG. 23
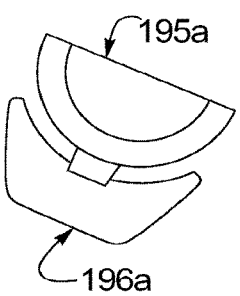
FIG. 24

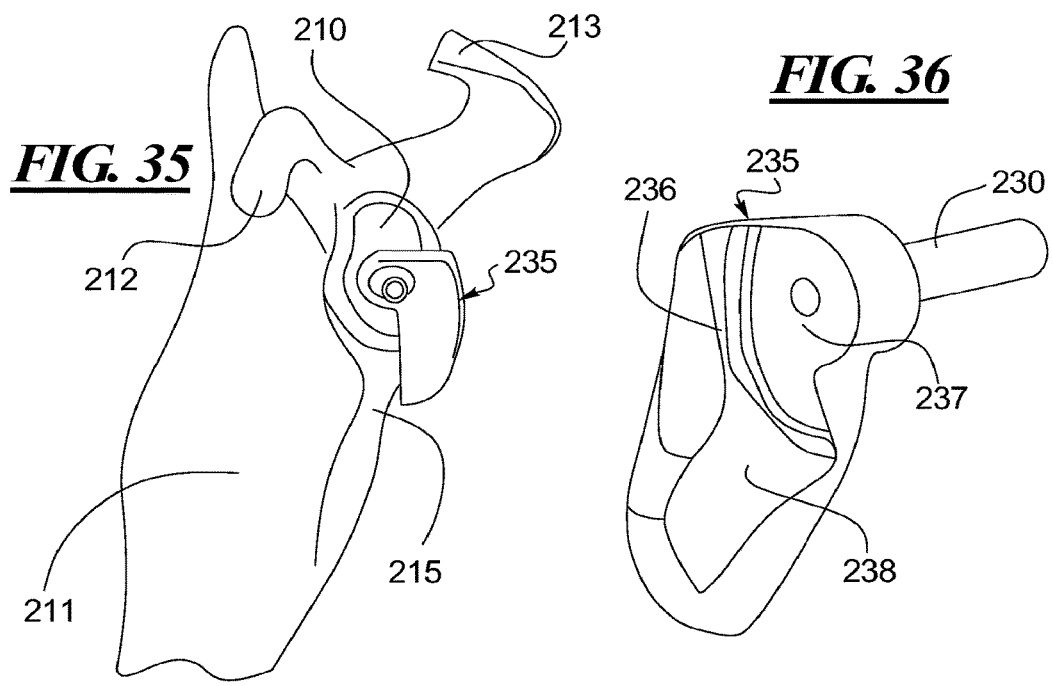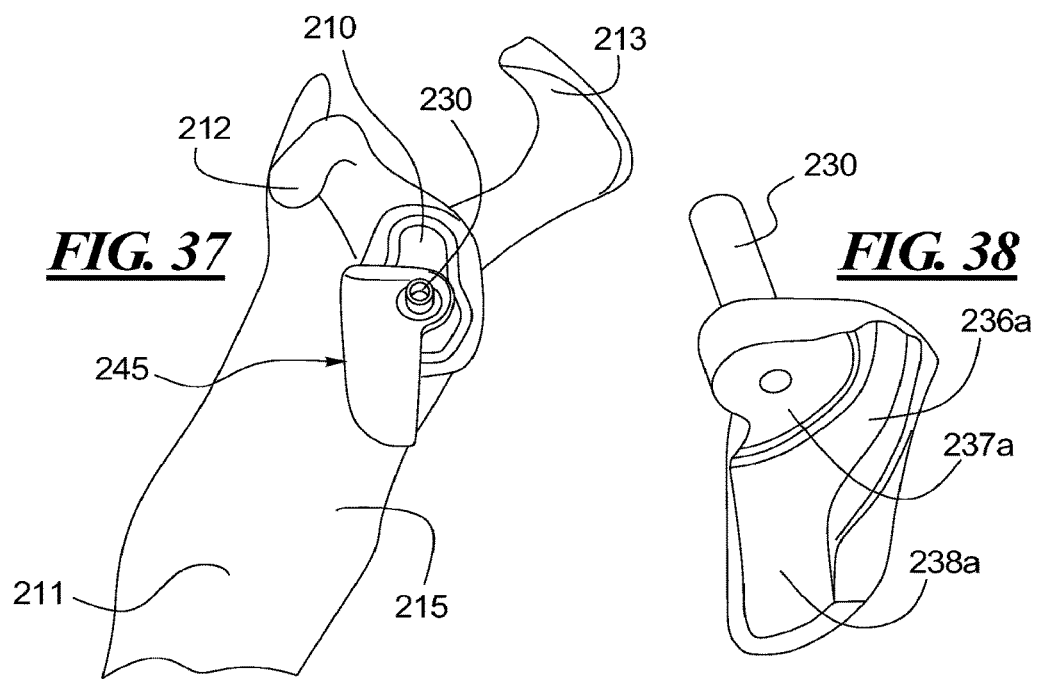

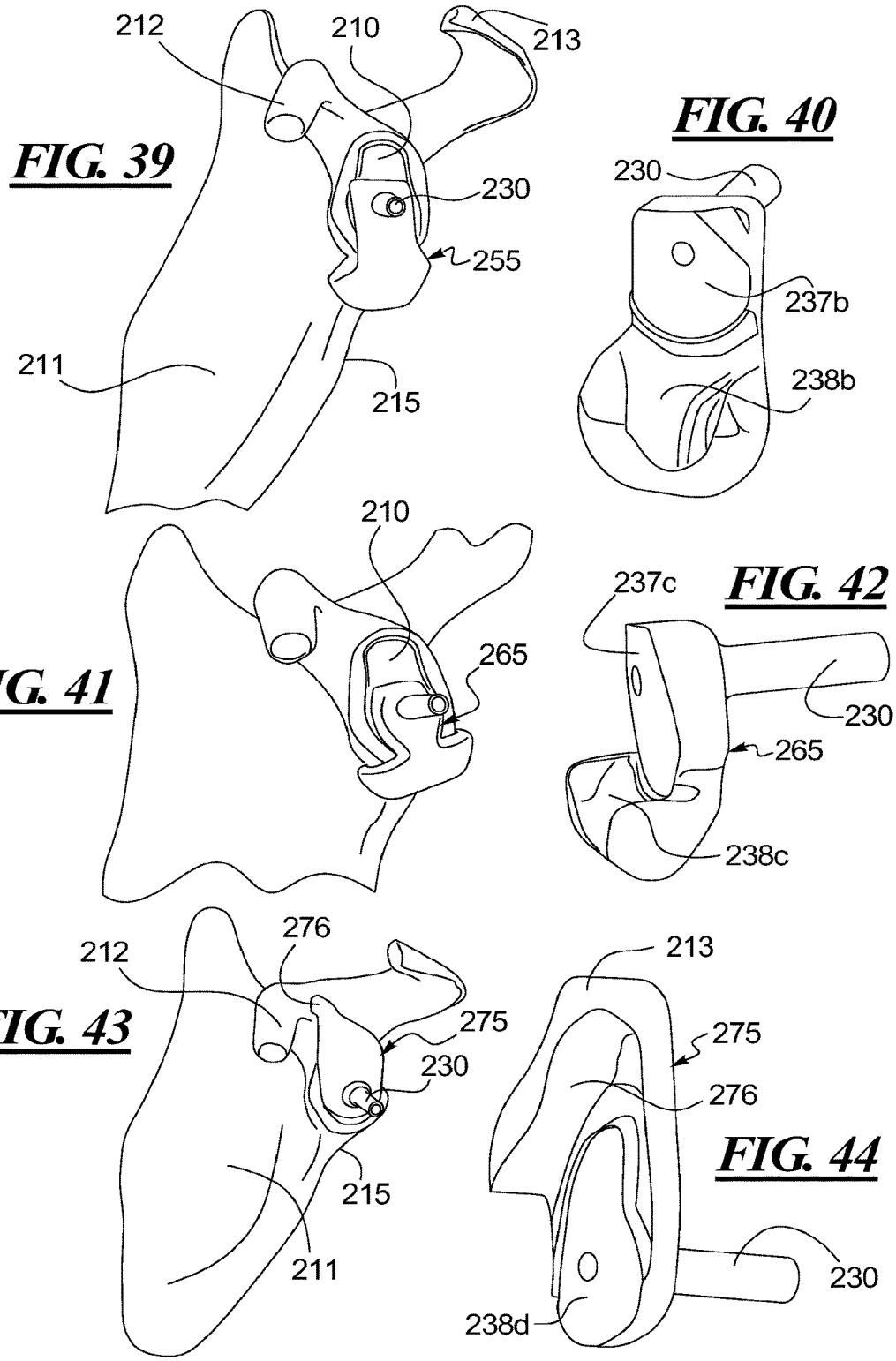

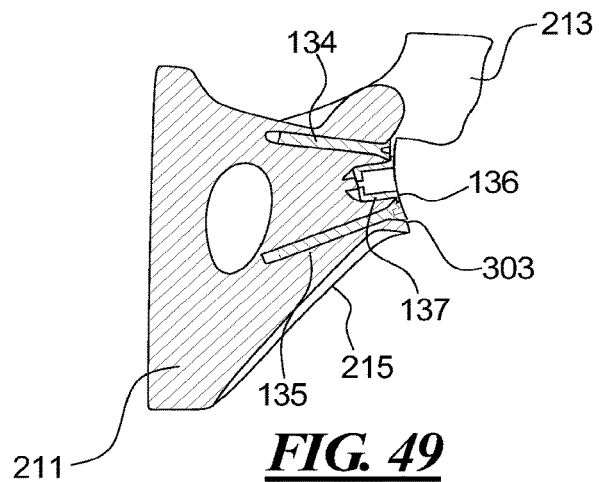
FIG. 49
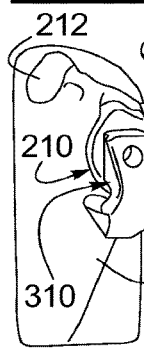 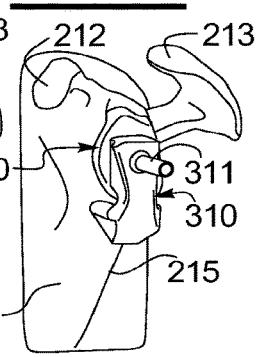 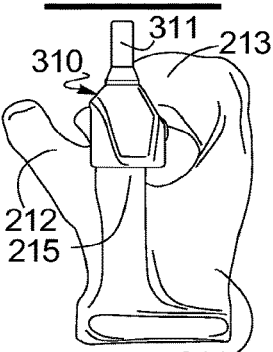 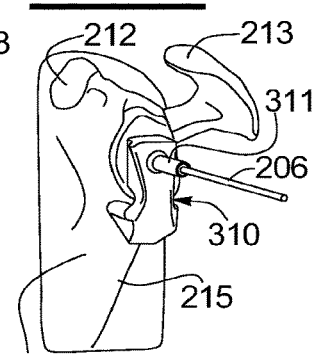
FIG. 50   FIG. 51   FIG. 52   FIG. 53
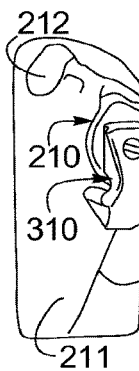 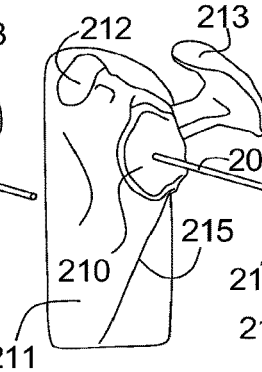 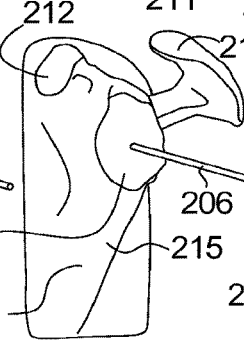 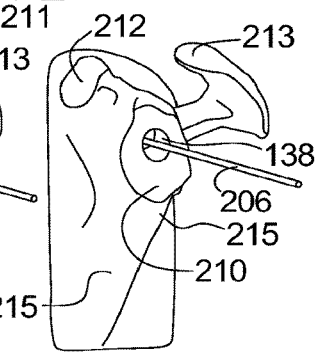
FIG. 54   FIG. 55   FIG. 56   FIG. 57

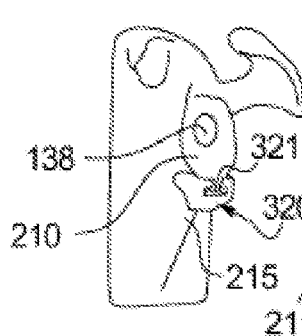
FIG. 58
FIG. 59
FIG. 60
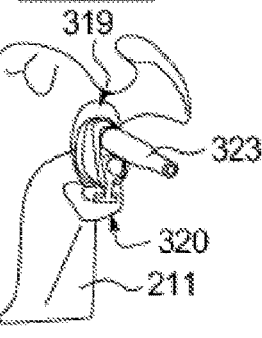
FIG. 61
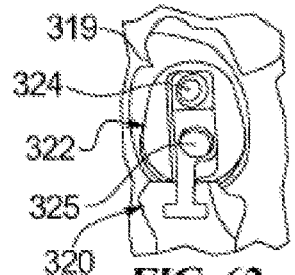
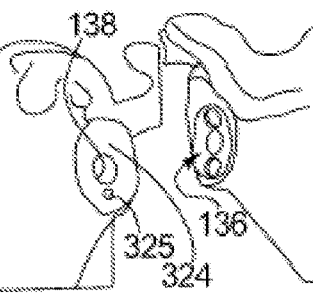
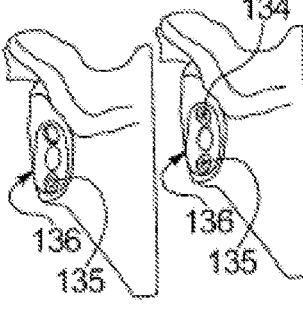
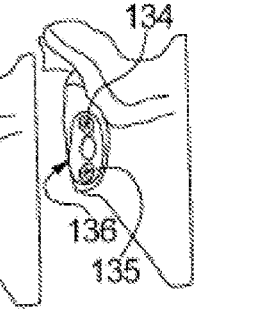
FIG. 62   FIG. 63   FIG. 64   FIG. 65   FIG. 66
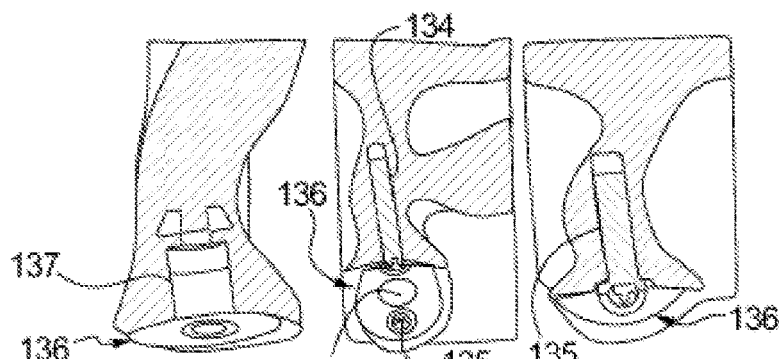
FIG. 67   FIG. 68   FIG. 69
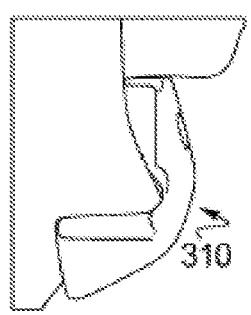
FIG. 70
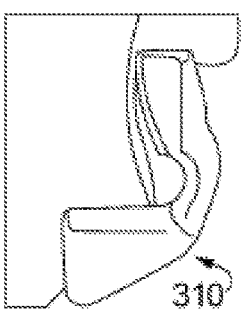
FIG. 71
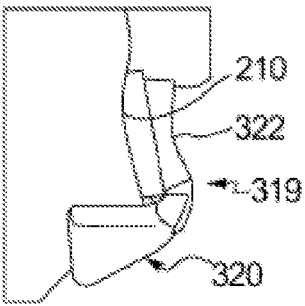
FIG. 72

METHODS AND DEVICES FOR INSTALLING STANDARD AND REVERSE SHOULDER IMPLANTS

CROSS REFERENCE TO RELATED APPLICATION

This application is a continuation of U.S. patent application Ser. No. 13/814,124 filed on Jun. 4, 2013, which is a U.S. National Phase Application of International Application No. PCT/US11/43719 filed on Jul. 12, 2011, which claims the benefit of U.S. Provisional Patent Application Ser. No. 61/373,092 filed on Aug. 12, 2010. The disclosures of each of these cross-referenced applications are incorporated herein by reference in their entirety.

DESCRIPTION

Technical Field

This disclosure relates generally to joint implants and more particularly to systems and methods for facilitating installations of various forms of shoulder implants that are specific to the anatomy of the patient.

Background

When a joint, such as a shoulder, hip or knee, becomes impaired due to arthritis, disease or trauma, it is sometimes necessary to replace all or part of the joint with one or more prostheses to restore function. Four anatomical characteristics that relate to shoulders are humeral and glenoid inclination and humeral retroversion and glenoid version, all of which can change as disease in the shoulder joint progresses.

For purposes of this disclosure, humeral inclination is defined as the angle between the plane of the anatomical neck of the proximal humerus and the metaphyseal axis of the humerus. Glenoid inclination is defined in the coronal plane as the angle between a line identifying the inferior-superior axis of the glenoid and a line connecting the intersection of the scapular spine with the medial border of the scapula and the middle of the spinoglenoid notch. Further, humeral retroversion (or humeral torsion) is defined as the angle between the normal vector to a plane defined by the perimeter of the anatomical neck and the transepicondylar axis of the distal humerus. Finally, glenoid version is defined in the axillary view as the angle between a line identifying the anterior-posterior rim of the glenoid cavity and a line perpendicular to a line identifying the scapular blade. Correction and modification of both humeral and glenoid inclination and version changes in diseased shoulder joints are benefits of successful shoulder implant procedures.

Anatomically, the average humeral inclination is approximately 135°, but can range from about 120° to about 150°. Average humeral retroversion is approximately 30°, but can range from about −5° to about 60°. Glenoid inclination can range from about 80° to about 100°, whereas glenoid version can range from about 0° to −14°. In order to optimize balancing of soft tissues and post-operative function, it is crucial to establish the proper inclination and version for each patient. Incorrect inclination and version can lead to problems including limited function, subsequent dislocations, and prosthetic component loosening and wear. Unfortunately, with existing implants and installation techniques, these critical parameters are chosen in a freehand manner.

In many cases, when an implant is used as treatment for an arthritic shoulder joint, it is necessary to remove or resect the diseased humeral head and prepare the proximal end of the humeral shaft to receive the stem, body, inclination set and head. It is important that the humeral head preparation be accurate so that position of the implant, which is determined in part by the configuration of the humeral head, replicates the original anatomic position of the humeral head.

In less severe cases, the humeral head may be resurfaced by installing an implant, that covers the humeral head after the humeral head has been resurfaced which removes abnormalities such as osteophytes, tuberositites, etc. In more severe cases, such as irreparable rotator cuff rupture, standard shoulder implants, as described above, would not provide sufficient pain-free joint stability or an adequate range of motion. Thus, an implant with a "reverse" joint has been developed where a base plate is attached to the glenoid fossa with screws after the glenoid fossa has been resurfaced. A head, sometimes referred to as a glenosphere, is attached to the glenoid base plate, as opposed to the humeral head. The humeral head is still resected and a stem is inserted downward into the intramedullary canal. A cup-shaped reverse body is attached to the proximal end of the stem, which receives a polymeric insert, receives the head or glenosphere that is fixed to the glenoid base plate.

The above procedures, while providing significant advancements, still suffer from certain drawbacks. For example, the most critical step in a humeral head resurfacing technique is placement of the initial guide wire, over which the humeral head resurfacing body slides. Unfortunately, the placement of the guidewire is performed using a freehand technique and an alignment tool. Contemporaneously, the surgeon estimates the desired inclination from the coronal (vertical) plane or transverse (horizontal) plane and maintains this desired inclination while the surgeon estimates a desired retroversion. Holding the head template in this exact position, the surgeon then drives the central guide wire or K-wire through the guide of the template using a drill or other suitable tool.

Thus, an optimal final positioning of the symmetrical implant on the asymmetrical humeral head is dependent on the surgeon's ability to visualize the desired orientation in three dimensions and the surgeon's ability to hold the head template steady while inserting the guide wire.

For traditional (non-reverse) shoulder implants, many surgeons use intramedullary cutting jigs or a freehand technique to resect the humeral head. For the more severe cases that require a reverse implant as described above, an intramedullary cutting jig is required to minimize the possibility of reaming with the incorrect retroversion, which could cause the screws that anchor the glenoid base plate to extend through or "break out" of the cortical bone structure of the glenohumeral joint or scapula. To avoid this problem, a complex intramedullary cutting jig is used.

SUMMARY OF THE DISCLOSURE

It would therefore be advantageous to replace as many freehand steps as possible with precise pre-determined and pre-fabricated templates and implants designed pre-operatively. It would also be advantageous to determine the desired retroversion and inclination pre-operatively.

Methods of resurfacing a humeral head and fabricating a humeral head template are disclosed that comprise obtaining a 3D scan of the humeral head. The 3D scan may be an MRI, a CT (CAT) scan or other suitable type of 3D scan, depending upon patient conditions and surgeon preference. From the 3D scan, patient specific anatomy is identified on the humeral head for purposes of stabilizing a humeral head template. A desired inclination and retroversion are also determined or identified based upon the one or more of the extent of patient's disease, the patient's anatomy and one or more determinations made by the surgeon as to the inclination and retroversion that can be achieved. A humeral head template is then fabricated based upon the 3D scan of the humeral head and the identified patient specific anatomy is used for stabilizing the humeral head template. A guide or boss is formed separately or as an integral part of the humeral head template for receiving a guide wire at the desired inclination and retroversion. To resurface the humeral head, the humeral head template is mounted on the humeral head with the guide and the guide wire is inserted through the guide and into the humeral head. The template is then removed over the guide wire and a humeral head implant is mounted over the guide wire and onto the humeral head where it is fixed using known procedures.

In an embodiment, patient specific anatomy for stabilizing a humeral head template may be selected from the group consisting of but not limited to: an articular surface; a diseased area on the articular surface; a bicipital groove; a greater tubercle; a lesser tubercle; a footprint of the greater tubercle; a metaphyseal axis; an anatomical neck; an anterior humeral head; a posterior humeral head; an anterior surgical neck; a posterior surgical neck; one or more soft tissue structure; and combinations thereof.

In another refinement, the determination of the inclination comprises determining a plane of the anatomical neck of the humeral head from the 3D scan, determining a metaphyseal axis from the 3D scan and determining a desired inclination from the angle between the plane of the anatomical neck and the metaphyseal axis.

In another refinement, the method the determining of at least one of the inclination and retroversion and further comprises determining a center point of the head of the humerus, determining a plane of an anatomical neck of the humerus from the three-dimensional scan; determining a line through the point and normal to the plane.

In another refinement, the determining of the inclination further comprises determining a center point of the head of the humerus, determining a plane of an anatomical neck from the three-dimensional scan, determining a line through the point and normal to the plane, determining a metaphyseal axis from the three-dimensional scan, and determining a desired inclination from the angle between the line and the metaphyseal axis.

In another refinement, the determining of the retroversion comprises determining a center point of the head of the humerus, determining a plane of an anatomical neck of the humerus from the three-dimensional scan, determining a line through the point and normal to the plane, acquiring an image of the humerus, determining the distal trans-epicondylar axis from the image, and determining a desired retroversion from the angle between the line and the distal trans-epicondylar axis.

A method for fabricating a cutting block for resecting a humeral head is also disclosed. The method comprises obtaining a three-dimensional scan of a proximal humerus, identifying patient specific anatomy on the proximal humerus, and fabricating a cutting block based upon the three-dimensional scan of the proximal humerus, and the identified patient specific anatomy.

In an embodiment, the fabricating of the cutting block further comprises determining a center point of the head of the humerus, determining a plane of an anatomical neck of the humerus from the three-dimensional scan, and determining a line through the point and normal to the plane.

In another refinement, the fabricating of the cutting block comprises determining the inclination. The method further comprises determining a center point of the head of the humerus, determining a plane of an anatomical neck from the three-dimensional scan, determining a line through the point and normal to the plane, determining a metaphyseal axis from the three-dimensional scan, and determining a desired inclination from the angle between the line and the metaphyseal axis.

In another refinement, the fabricating of the cutting block comprises determining the retroversion. The fabrication comprises determining a center point of the head of the humerus, determining a plane of an anatomical neck of the humerus from the three-dimensional scan, determining a line through the point and normal to the plane, acquiring an image of the humerus, determining the distal trans-epicondylar axis from the image, and determining a desired retroversion from the angle between the line and the distal trans-epicondylar axis.

In another refinement, the determination of the desired retroversion comprises determining a plane of the anatomical neck of the humeral head from the 3D scan. A superior-inferior x-ray of the humeral head and elbow that exposes the distal epicondylar axis from the x-ray is taken to provide an estimation of the existing retroversion and a desired retroversion is determined from an axis of the humerus.

In another refinement, a superior-inferior x-ray of the humeral head and distal epicondylar axis are taken and used with three-dimensional scan to determine the desired retroversion.

In an embodiment, the determining of the retroversion comprises determining a center point of the head of the humerus, determining a plane of an anatomical neck of the humerus from the three-dimensional scan, determining a line through the point and normal to the plane, acquiring an image of the humerus, determining the distal trans-epicondylar axis from the image, and determining a desired retroversion from the angle between the line and the distal trans-epicondylar axis.

In an embodiment, the humeral head template may be mounted and fixed to the humeral head without reaming the humeral head. In another refinement, the humeral head is reamed to provide a spherical surface for receiving a humeral head implant.

In an embodiment, a marker is used transversely across the patient's elbow that marks the distal epicondylar axis, which is used with the superior-inferior x-ray to determine the existing retroversion and the desired retroversion angle of the implant.

In an embodiment, the humeral head implant is fabricated with a spherical outer surface based upon the 3D scan of the humeral head and the identified patient specific anatomy for stabilizing the humeral head template at the desired inclination and retroversion.

In another refinement, an axis of the guide wire and/or guide for receiving the guide wire are adjusted based upon one or more conditions of the glenoid fossa.

Methods for resecting humeral heads and for fabricating patient specific cutting blocks for humeral head resections are also disclosed. One disclosed method comprises obtaining a 3D scan of a humeral head. Patient specific anatomy is identified on the humeral head, proximally of the anatomical neck or distally of the humeral head and anatomical neck for stabilizing a cutting block on the humeral head. A cutting block is fabricated based upon the 3D scan of the humeral head, which may also include portions of the humerus distal to the humeral head, such as the metaphyseal cylinder or flute, and negative geometry of the identified patient specific anatomy is used in fabricating the cutting block for purposes of stabilizing the cutting block on the humeral head. The cutting block is then attached to the humeral head. The cutting block presents a resection plane and resection of the humeral head is accomplished using the cutting block as a guide.

In an embodiment, patient specific anatomy for fabricating a patient specific cutting block and stabilizing a cutting block on a humeral head may selected from the group consisting of but not limited to: an anterior portion of the proximal humerus; a superior portion of the proximal humerus; an inferior portion of the proximal humerus; a tuberositite; an osteophyte; a biceps groove; a soft tissue insertion point; and combinations thereof.

In an embodiment, the cutting block is attached to the humeral head or a proximal portion of the humerus using one or more fasteners selected from the group consisting of bone spikes, trocar pins, speed pins, bone screws and combinations thereof.

In an embodiment, the cutting block may attached to the proximal humeral head, the distal humeral head, a portion of the humeral head distally of the anatomical neck of the humeral head or a portion of the metaphyseal shaft. Other patient specific locations for attaching the cutting block will be apparent to those skilled in the art and the disclosed methods are not limited to the locations recited here.

Methods for resecting humeral heads and fabricating cutting blocks are also disclosed that are designed for reverse shoulder implant procedures. The methods include obtaining a 3D scan of the humeral head and identifying an anatomical neck of the humeral head in a vector normal to the anatomical neck. The distal epicondylar axis is identified using a superior-inferior x-ray of the humeral head and the elbow that has been marked with a marker that extends transversely across the elbow along the epicondylar axis. A resection plane is selected through the humeral head at an angle of about 65° from the epicondylar axis (or a resection plane of about 155° from the horizontal or coronal plane). A cutting block is fabricated based upon the 3D scan and the negative geometry of the identified patient specific anatomy for stabilizing the cutting block at the desired resection plane. The cutting block is then attached to the humeral head at the desired resection plane. Resection is carried out using the cutting block as a guide.

In an embodiment, the patient specific anatomy for cutting blocks for reverse shoulder implants is selected from the group consisting of but not limited to: an anterior portion of the proximal humerus; a superior portion of the proximal humerus; an inferior portion of the proximal humerus; a tuberositite; an osteophyte; a biceps groove; a soft tissue insertion point; and combinations thereof.

In an embodiment, the cutting block may be attached to the humeral head using one or more fastening elements as described above. In an embodiment, the cutting block is attached to the proximal humeral head, distal humeral head, and a portion of the humeral head distal to the anatomical neck or the metaphyseal shaft. Other patient specific locations for attaching the cutting block will be apparent to more skilled in the art and the disclosed methods are not limited to the locations recited here.

In an embodiment, a jig or apparatus is also disclosed for performing the 3D scan and superior-inferior axial x-ray of the humerus while maintaining proper position of the patient's arm and shoulder. A first plate with a first holder is used to hold the patient's arm in place between the patient's elbow and the humeral head. A second plate perpendicular to the first plate and including a second holder for holding the patient's elbow is also provided and further includes at least one additional holder for holding at least a portion of the patient's hand or wrist in place during the procedure.

Methods for fabricating glenoid templates for inserting a guide wire at a desired trajectory during a resurfacing of a glenoid fossa are also disclosed. One method comprises: obtaining a three-dimensional scan of a scapula; identifying patient specific anatomy on the scapula; determining a plane of the glenoid fossa; fabricating the glenoid template based upon the three-dimensional scan of the scapula, the identified patient specific anatomy; and forming a guide on the glenoid template for receiving a guide wire at a desired location, inclination and version.

In an embodiment, the determining of at least one of the location, inclination and version comprises determining a desired center point on the glenoid fossa, determining a plane of a glenoid of the scapula from the three-dimensional scan, and determining a line through the point and normal to the plane.

In another refinement, the determining of at least one of the desired location, inclination and version further comprises determining an optimal placement of an implant assembly on the three-dimensional scan.

In an embodiment, the determining of the inclination comprises: determining a first point at the intersection of the scapula spine and the medial border of the scapula; determining a second point at the middle of the spinoglenoid notch; determining a first line through the first and second points; determining a third point at the superior margin of the glenoid fossa; determining a forth point at the inferior margin of the glenoid fossa; determining a second line through the third and fourth points; and determining a desired inclination from an angle between the first and second lines.

In an embodiment, the determining of the version comprises determining a first point at the anterior margin of the glenoid fossa, determining a second point at the posterior margin of the glenoid fossa, determining a first line through the first and second points, determining a third point at the midpoint of the glenoid fossa, determining a forth point at the vertebral border of the scapula, determining a second line through the third and fourth points; determining a third line which is perpendicular to the second line; and determining a desired version from an angle between the first and third lines.

In an embodiment, the axis of the guide wire may be adjusted based on one or more conditions of a humeral head or soft tissue structure.

Methods for resurfacing glenoid fossas, methods for fabricating patient specific blocks referred to as glenoid blocks for inserting guide wires into glenoid fossas and glenoid fossa drill guides are also disclosed. The surgical techniques for preparing the glenoid fossa for a reverse shoulder implant and for a standard shoulder implant are different. For a standard implant, one disclosed method includes obtaining a 3D scan of the glenoid fossa and identifying patient specific anatomy on the glenoid fossa for purposes of stabilizing a glenoid block that is used for inserting a guide wire into the center of the glenoid fossa. A determination of an original plane of the glenoid fossa prior to the onset of disease is also made. The guide wire may be inserted at an intersection of the superior-inferior and anterior-posterior axis for standard implants. A patient specific glenoid block is fabricated from the 3D scan.

In an embodiment, a method of resurfacing a glenoid fossa comprises obtaining a force-dimensional scan of a scapula. Patient specific anatomy on the scapula is identified. A desired location, inclination and version are identified. Fabricating a template based upon the three-dimensional scan of the scapula, the identified patient specific anatomy and forming a guide on the template for receiving a guide wire at the desired location, inclination and version. Then, the template is mounted onto the scapula, inserting the guide wire through the guide and into the glenoid fossa, removing the template, inserting at least one instrument over the guide wire to prepare the glenoid for receiving an implant, removing the instrument and the guide wire; and mounting the glenoid implant to the glenoid fossa.

In an embodiment, the determining of at least one of the inclination and version further comprises determining a desired center point on the glenoid fossa, determining a plane of a glenoid of the scapula from the three-dimensional scan, and determining a line through the point and normal to the plane.

In another refinement, the determining of the inclination comprises determining a first point at the intersection of the scapula spine and the medial border of the scapula, determining a second point at the middle of the spinoglenoid notch, determining a first line through the first and second points, determining a third point at the superior margin of the glenoid fosse, determining a forth point at the inferior margin of the glenoid fossa, determining a second line through the third and fourth points, and determining a desired inclination from an angle between the first and second lines.

In another refinement, the determining of the version comprises determining a first point at the anterior margin of the glenoid fossa, determining a second point at the posterior margin of the glenoid fossa, determining a first line through the first and second points, determining a third point at the midpoint of the glenoid fossa, determining a forth point at the vertebral border of the scapula, determining a second line through the third and fourth points, determining a third line which is perpendicular to the second line, and determining a desired version from an angle between the first and third lines.

In another refinement, the glenoid fossa is reamed prior to mounting the glenoid template onto the glenoid fossa.

For reverse implants, the guide wire may be inserted slightly posteriorly and inferiorly to the intersection and the glenoid block is fabricated with this concept in consideration. Further, the surgeon may desire to insert the guide wire into the glenoid fossa along an axis that ranges from 0° to 10° inferiorly from the plane of the original pre-diseased glenoid fossa. Again, the glenoid block and guide wire guide can be fabricated with these concepts in consideration. The appropriately fabricated glenoid block is mounted on to the glenoid fossa and the guide wire is inserted through the guide of the glenoid block at the desired angle before the glenoid block and guide are removed. A central hole is drilled into the glenoid fossa for purposes of receiving the central peg of the glenoid base plate. A cannulated drill is used to drill the central over the guide wire.

A drill guide may mounted in the center hole and positioned by the surgeon before peripheral holes are drilled through the drill guide for receiving the locking screws. The glenoid base plate may be fixed to the glenoid fossa with fasteners that extend through the peripheral holes.

The patient specific anatomy for supporting the glenoid block in place during the guide wire insertion procedure for both standard and reverse implants may be selected from the group consisting of, but not limited to: an anterior face of the glenoid, a posterior face of the glenoid, a medial face of the glenoid, a portion of the scapular neck, a medial hard stop on the glenoid face, a posterior face of the glenoid, a junction of a coracoid and the glenoid face, and combinations thereof.

In an embodiment, the glenoid fossa is reamed after the drilling of the central hole for the central peg of the glenoid base plate or glenoid implant and prior to the mounting of the drill guide on the glenoid fossa.

One disclosed method for reverse implant procedures includes obtaining a 3D scan of the glenoid fossa and identifying patient specific anatomy on the glenoid fossa for purposes of stabilizing the glenoid block. A determination of an original plane of the glenoid fossa prior to the onset of disease is also made. Instead of inserting the guide wire through an intersection of the superior-inferior and anterior-posterior axis, the guide wire is inserted slightly posteriorly and inferiorly to this intersection and the glenoid block is made with this concept in consideration. Further, the surgeon may desire the guide wire to be inserted into the glenoid fossa along an axis that ranges from 0° to 10° from the plane of the original pre-diseased glenoid fossa. Again, the glenoid block and guide wire guide can be made with these concepts in consideration. The appropriately fabricated glenoid block is mounted on to the glenoid fossa and the guide wire is inserted through the guide of the glenoid block at the desired angle before the glenoid block and guide are removed. A central hole is drilled into the glenoid fossa for purposes of receiving the central peg of a glenoid base plate, which is held in place by locking screws as opposed so a glenoid implant, which may be cemented in place. A cannulated drill is used to drill the central hole over the guide wire. A drill guide is mounted in the center hole and positioned by the surgeon before peripheral holes are drilled through the drill guide for receiving the locking screws. The glenoid base plate is then fixed to the glenoid fossa with fasteners that extend through the peripheral holes.

In an embodiment, the glenoid fossa is reamed after the drilling of the central hole for the central peg and prior to the mounting of the drill guide on the glenoid fossa.

Another more specialized procedure for a reverse shoulder implant is also disclosed along with a two-piece bone screw drill guide. This procedure and the two-piece bone screw drill guide are intended to further reduce the possibility of breakout or an extension of the locking screws through the scapular cortical bone. Such a procedure includes using a two-piece bone screw drill guide that includes an inferior bone screw drill guide and a superior bone screw drill guide that are coupled together in a manner so to provide some lateral movement of the superior bone screw drill guide with respect to the glenoid fossa during the drilling process.

Patient specific anatomy on an inferior portion of the glenoid fossa is identified for purposes of stabilizing the inferior bone screw drill guide at the inferior end of the glenoid fossa. The superior bone screw drill guide is also fabricated based upon the 3D scan that can be removably coupled to the inferior bone screw drill guide to form the two-piece bone screw drill guide. Peripheral holes for accommodating locking screws are then drilled through the superior bone screw drill guide. The superior bone screw drill guide is then removed from the inferior bone screw drill guide. A glenoid base plate is then fixed to the glenoid fossa with fasteners that extend through the peripheral holes and the central peg of the glenoid base plate is received in the central hole drilled with the cannulated drill as described above.

In another refinement, the glenoid fossa is reamed after removal of the glenoid block before or after the drilling of the central hole over the guide wire.

In another refinement, the patient specific anatomy for stabilizing the inferior bone screw drill guide is selected from the group consisting of, but not limited to: an intraglenoid tubercule; a scapular pillar; one or more portions of the glenoid face; and combinations thereof.

In another refinement, a two-piece drill guide is used to drill the peripheral holes for the peripheral pegs of a glenoid implant that is cemented to the glenoid fossa during a standard implant procedure. The two-piece drill guide for the standard implant procedure includes an inferior drill guide slidably coupled to a superior drill guide. The inferior drill guide is fabricated based on the 3D scan an is stabilized at the inferior end of the glenoid fossa using patient specific anatomy selected from the group consisting of, but not limited to: an intraglenoid tubercule; a scapular pillar; one or more portions of the glenoid face; and combinations thereof.

There is provided a method of fabricating a template used in a humeral head resurfacing procedure, the method comprising: obtaining a three-dimensional scan of a proximal humerus; identifying patient specific anatomy on the proximal humerus; determining a desired location, inclination and retroversion; fabricating the template based upon the three-dimensional scan of the proximal humerus, the identified patient specific anatomy; and forming a guide on the template for receiving a guide wire at the desired location, inclination and retroversion.

In some embodiments, the patient specific anatomy is selected from the group consisting of an articular surface, a diseased area on the articular surface, a bicipital groove, a greater tubercle, a lesser tubercle, a footprint of the greater tubercle, a metaphyseal axis, a trans-epicondylar axis, an anatomical neck, an anterior portion of the proximal humerus, a posterior portion of the proximal humerus, an osteophite, one or more soft tissue structures and combinations thereof.

In some embodiments, the step of determining of at least one of the inclination and retroversion further comprises: determining a center point of the head of the humerus; determining a plane of an anatomical neck of the humerus from the three-dimensional scan; and determining a line through the point and normal to the plane.

In some embodiments, she step of determining of the inclination comprises: determining a center point of the head of the humerus; determining a plane of an anatomical neck of the humerus from the three-dimensional scan; determining a line through the point and normal to the plane; determining a metaphyseal axis from the three-dimensional scan; and determining a desired inclination from an angle between the line and the metaphyseal axis.

In some embodiments, the step of determining of the retroversion comprises: determining a center point of the head of the humerus; determining a plane of an anatomical neck of the humerus from the three-dimensional scan; determining a line through the point and normal to the plane; acquiring an image of the humerus; determining a distal trans-epicondylar axis from the image; and determining a desired retroversion from an angle between the line and the distal trans-epicondylar axis.

In some embodiments, the method further comprises taking a superior-inferior x-ray of the humeral head and distal trans-epicondylar axis and using the x-ray and the three-dimensional scan to determine a desired retroversion.

In some embodiments, the method further comprises adjusting an axis of the guide wire based on one or more conditions of a glenoid fossa.

There is provided a method of resurfacing a humeral head, the method comprising: obtaining a three-dimensional scan of a humerus; identifying patient specific anatomy on the humerus; determining a desired location, inclination and retroversion; fabricating a template based upon the three-dimensional scan of the humerus and the identified patient specific anatomy; forming a guide on the template for receiving a guide wire at the desired location, inclination and retroversion; mounting the template onto the humeral head; inserting the guide wire through the guide and into the humeral head; removing the template; inserting an instrument over the guide wire to prepare the head for receiving an implant; removing the instrument and the guide wire; and mourning the implant to the humeral head.

In some embodiments, the patient specific anatomy is selected from the group consisting of an articular surface, a diseased area on the articular surface, a bicipital groove, a greater tubercle, a lesser tubercle, a footprint of the greater tubercle, a metaphyseal axis, a trans-epicondylar axis, an anatomical neck, an anterior portion of the proximal humerus, a posterior portion of the proximal humerus, an osteophite, one or more soft tissue structures and combinations thereof.

In some embodiments, the method further comprises the step of determining of at least one of the inclination and retroversion further comprises: determining a center point of the head of the humerus; determining a plane of an anatomical neck of the humerus from the three-dimensional scan; and determining a line through the point and normal to the plane.

In some embodiments, the step of determining of the inclination comprises: determining a center point of the head of the humerus; determining a plane of an anatomical neck from the three-dimensional scan; determining a line through the point and normal to the plane; determining a metaphyseal axis from the three-dimensional scan; and determining a desired inclination from an angle between the line and the metaphyseal axis.

In some embodiments, the step of determining of the retroversion comprises: determining a center point of the head of the humerus; determining a plane of an anatomical neck of the humerus from the three-dimensional scan; determining a line through the point and normal to the plane; acquiring an image of the humerus; determining a distal trans-epicondylar axis from the image; and determining a desired retroversion from an angle between the line and the distal trans-epicondylar axis.

In some embodiments, the method further comprises taking a superior-inferior x-ray of the humeral head and distal trans-epicondylar axis and using the x-ray and the three-dimensional scan to determine a desired retroversion.

In some embodiments, the method further comprises adjusting an axis of the guide wire based on one or more conditions of a glenoid fossa.

There is provided a method for fabricating a cutting block for resecting a humeral head, the method comprising: obtaining a three-dimensional scan of a proximal humerus; identifying patient specific anatomy on the proximal humerus; and fabricating the cutting block based upon the three-dimensional scan of the proximal humerus, and the identified patient specific anatomy.

In some embodiments, the patient specific anatomy is selected from the group consisting of an articular surface, a diseased area on the articular surface, a bicipital groove, a greater tubercle, a lesser tubercle, a footprint of the greater tubercle, a metaphyseal axis, a trans-epicondylar axis, an anatomical neck, an anterior portion of the proximal humerus, a posterior portion of the proximal humerus, an osteophite, one or more soft tissue structures and combinations thereof.

In some embodiments, the step of fabricating the cutting block comprises: determining a center point of the head of the humerus; determining a plane of the anatomical neck of the humerus from the three-dimensional scan; and determining a line through the point and normal to the plane.

In some embodiments, the step of determining the inclination comprises: determining a center point of the head of the humerus; determining a plane of the anatomical neck from the three-dimensional scan; determining a line through the point and normal to the plane; determining a metaphyseal axis from the three-dimensional scan; and determining a desired inclination from an angle between the line and the metaphyseal axis.

In some embodiments, the step of determining the retroversion comprises: determining a center point of the head of the humerus; determining a plane of the anatomical neck of the humerus from the three-dimensional scan; determining a line through the point and normal to the plane; acquiring an image of the humerus; determining a distal trans-epicondylar axis from the image; and determining a desired retroversion from an angle between the line and the distal trans-epicondylar axis.

There is provided a method for resecting a humeral head, the method comprising: obtaining a three-dimensional scan of a proximal humerus; identifying patient specific anatomy on the proximal humerus; fabricating a cutting block based upon the three-dimensional scan of the proximal humerus, and the identified patient specific anatomy; attaching the cutting block to the proximal humerus; and resecting the humeral head using the cutting block as a guide.

In some embodiments, the patient specific anatomy is selected from the group consisting of an articular surface, a diseased area on the articular surface, a bicipital groove, a greater tubercle, a lesser tubercle, a footprint of the greater tubercle, a metaphyseal axis, a trans-epicondylar axis, an anatomical neck, an anterior portion of the proximal humerus, a posterior portion of the proximal humerus, an osteophite, one or more soft tissue structures and combinations thereof.

In some embodiments, the cutting block is attached to the humeral head using one or more fasteners selected from the group consisting of bone spikes, trocar pins, speed pins, bone screws and combinations thereof.

In some embodiments, the step of fabricating the cutting block comprises determining a center point of the head of the humerus; determining a plane of an anatomical neck of the humerus from the three-dimensional scan; and determining a line through the point and normal to the plane.

In some embodiments, the step of determining the inclination comprises: determining a center point of the head of the humerus; determining a plane of an anatomical neck from the three-dimensional scan; determining a line through the point and normal to the plane; determining a metaphyseal axis from the three-dimensional scan; and determining a desired inclination from an angle between the line and the metaphyseal axis.

In some embodiments, the step of determining the retroversion comprises: determining a center point of the head of a humerus; determining a plane of an anatomical neck of the humerus from the three-dimensional scan; determining a line through the point and normal to the plane; acquiring an image of the humerus; determining a distal trans-epicondylar axis from the image; and determining a desired retroversion from an angle between the line and the distal trans-epicondylar axis.

There is provided a method for fabricating a glenoid template for inserting a guide wire at a desired trajectory during a resurfacing of a glenoid fossa, the method comprising: obtaining a three-dimensional scan of a scapula; identifying patient specific anatomy on the scapula; determining a plane of the glenoid fossa; fabricating the glenoid template based upon the three-dimensional scan of the scapula, the identified patient specific anatomy; and forming a guide on the glenoid template for receiving a guide wire at a desired location, inclination and version.

In some embodiments, the first piece of the guide is fabricated based on patient specific anatomy selected from the group consisting of a face of the glenoid fossa, a diseased area on a face of the glenoid fossa, an anterior rim of glenoid, a posterior rim of glenoid, an inferior rim of glenoid, a superior rim of glenoid, an infraglenoid tubercle, a supraglenoid tubercle, a scapula neck, a scapula blade, a coracoid spine, a scapula spine, a midpoint of the glenoid fossa, one or more soft tissue structures, and combinations thereof.

In some embodiments, the step of determining of at least one of the location, inclination and version comprises determining a desired center point on the glenoid fossa; determining a plane of a glenoid of the scapula from the three-dimensional scan; determining a line through the point and normal to the plane.

In some embodiments, the step of determining of at least one of the desired location, inclination and version further comprises: determining an optimal placement of an implant assembly on the three-dimensional scan.

In some embodiments, the step of determining of the inclination comprises: determining a first point at the intersection of the scapula spine and the medial border of the scapula; determining a second point at the middle of the spinoglenoid notch; determining a first line through the first and second points; determining a third point at the superior margin of the glenoid fossa; determining a forth point at the inferior margin of the glenoid fossa; determining a second line through the third and fourth points; determining a desired inclination from an angle between the first and second lines.

In some embodiments, the method further includes the step of determining version comprising: determining a first point at an anterior margin of the glenoid fossa; determining a second point at the posterior margin of the glenoid fossa; determining a first line through the first and second points; determining a third point at the midpoint of the glenoid fossa; determining a forth point at the vertebral border of the scapula; determining a second line through the third and fourth points; determining a third line, which is perpendicular to the second line; and determining a desired version from an angle between the first and third lines.

In some embodiments, the method further includes adjusting an axis of the guide wire based on one or more conditions of a humeral head or soft tissue structure.

There is provided a method of resurfacing a glenoid fossa, the method comprising: obtaining a three-dimensional scan of a scapula; identifying patient specific anatomy on the scapula; determining a desired location, inclination and version; fabricating a template based upon the three-dimensional scan of the scapula, the identifiers patient specific anatomy and forming a guide on the template for receiving a guide wire at the desired location, inclination and version;

mounting the template onto the scapula; inserting the guide wire through the guide and into the glenoid fossa; removing the template; inserting at least one instrument over the guide wire to prepare the glenoid for receiving an implant; removing the instrument and the guide wire; and mounting a glenoid implant to the glenoid fossa.

In some embodiments, the first piece of the guide is fabricated based on patient specific anatomy selected from the group consisting of a face of the glenoid fossa, a diseased area on a face of the glenoid fossa, an anterior rim of glenoid, a posterior rim of glenoid, an inferior rim of glenoid, a superior rim of glenoid, an infraglenoid tubercle, a supraglenoid tubercle, a scapula neck, a scapula blade, a coracoid spine, a scapula spine, a midpoint of the glenoid fossa, one or more soft tissue structures, and combinations thereof.

In some embodiments the step of determining of at least one of the inclination and version further comprises: determining a desired center point on the glenoid fossa; determining a plane of a glenoid of the scapula from the three-dimensional scan; and determining a line through the point and normal to the plane.

In some embodiments the step of determining inclination comprises: determining a first point at the intersection of the scapula spine and the medial border of the scapula; determining a second point at the middle of the spinoglenoid notch; determining a first line through the first and second points; determining a third point at the superior margin of the glenoid fossa; determining a forth point at the inferior margin of the glenoid fossa; determining a second line through the third and fourth points; and determining a desired inclination from an angle between the first and second lines.

In some embodiments the step of determining version comprises: determining a first point at an anterior margin of the glenoid fossa; determining a second point at the posterior margin of the glenoid fossa; determining a first line through the first and second points; determining a third point at the midpoint of the glenoid fossa; determining a forth point at the vertebral border of the scapula; determining a second line through the third and fourth points; determining a third line which is perpendicular to the second line; and determining a desired version from an angle between the first and third lines.

In some embodiments, the glenoid fossa is reamed prior to mounting the glenoid template onto the glenoid fossa.

There is provided a method for fabricating a two-piece drill guide for preparing a glenoid fossa, the method comprising: obtaining a three-dimensional scan of a scapula; identifying patient specific anatomy on a scapula; determining a desired location, inclination and version; fabricating a first piece of the drill guide based on the patient specific anatomy; fabricating a second piece of the drill guide based on the desired location, inclination and version; and coupling the first and second pieces of the drill guide.

In some embodiments, the first piece of the drill guide is fabricated based on patient specific anatomy selected from the group consisting of a face of the glenoid fossa, a diseased area on a face of the glenoid fossa, an anterior rim of glenoid, a posterior rim of glenoid, an inferior rim of glenoid, a superior rim of glenoid, an infraglenoid tubercle, a supraglenoid tubercle, a scapula neck, a scapula blade, a coracoid spine, a scapula spine, a midpoint of the glenoid fossa, one or more soft tissue structures, and combinations thereof.

In some embodiments, the first piece of the drill guide is coupled to the second piece of the drill guide using a dovetail type or T-slot type connection that enables the second piece of the guide to move medially with respect to the first piece of the guide.

STATEMENTS OF THE INVENTION

One disclosed method of fabricating a template used in a resurfacing procedure of a humeral head comprises:
  identifying patient specific anatomy from a three-dimensional scan of the proximal humerus;
  determining at least one of a desired location, inclination and retroversion;
  fabricating a template based upon the three-dimensional scan of the proximal humerus and the identified patient specific anatomy; and
  forming a guide on the template for receiving a guide wire at the desired location, inclination and retroversion.

The disclosed methods may further comprise:
  fabricating a cutting block for resecting the humeral head based upon the three-dimensional scan of the proximal humerus and the identified patient specific anatomy.

In the disclosed methods, the patient specific anatomy is selected from the group consisting of an articular surface, a diseased area on the articular surface, a bicipital groove, a greater tubercle, a lesser tubercle, a footprint of the greater tubercle, metaphyseal axis, a trans-epicondylar axis, an anatomical neck, an anterior portion of the proximal humerus, a posterior portion of the proximal humerus, an osteophite, one or more soft tissue structures and combinations thereof.

In the disclosed methods, the determining of at least one of a desired location, inclination and retroversion and further comprises:
  determining a center point of the humeral head;
  determining a plane of an anatomical neck of the proximal humerus from the three-dimensional scan; and
  determining a line through the center point and normal to the plane.

In the disclosed methods, the determining of at least one of a desired location, inclination and retroversion and further comprises:
  determining a center point of the humeral head;
  determining a plane of an anatomical neck of the proximal humerus from the three-dimensional scan;
  determining a line through the center point and normal to the plane;
  determining a metaphyseal axis from the three-dimensional scan; and
  determining a desired inclination from an angle between the line and the metaphyseal axis.

In the disclosed methods, the determining of at least one of a desired location, inclination and retroversion and further comprises:
  determining a center point of the humeral head;
  determining a plane of an anatomical neck of the proximal humerus from the three-dimensional scan;
  determining a line through the center point and normal to the plane;
  determining a distal trans-epicondylar axis from an image of the humerus; and
  determining a desired retroversion from an angle between the line and the distal trans-epicondylar axis.

In the disclosed methods, the determining of at least one of a desired location, inclination and retroversion and further comprises:

determining a desired retroversion and a distal transepicondylar axis from a superior-inferior x-ray of the humeral head;

determining a desired retroversion from the superior-inferior x-ray and the three-dimensional image of the humeral head.

The disclosed methods may further comprise adjusting an axis of the guide wire based on one or more conditions of a glenoid fossa.

Another disclosed method for fabricating a glenoid template for inserting a guide wire at a desired trajectory during a resurfacing of a glenoid fossa comprises:

identifying patient specific anatomy on a scapula from a three-dimensional scan of the scapula;

determining a plane of the glenoid fossa from the three-dimensional scan of the scapula;

determining a desired location, inclination and version from the three-dimensional scan of the scapula;

fabricating the glenoid template based upon the three-dimensional scans of the scapula and the identified patient specific anatomy; and forming a guide on the glenoid template for receiving the guide wire at the desired location, inclination and version.

In the disclosed methods, a first piece of the guide is fabricated based on patient specific anatomy selected from the group consisting of a face of the glenoid fossa, a diseased area on a face of the glenoid fossa, an anterior rim of glenoid, a posterior rim of glenoid, an inferior rim of glenoid, a superior rim of glenoid, an infraglenoid tubercle, a supraglenoid tubercle, a scapula neck, a scapula blade, a coracoid spine, a scapula spine, a midpoint of the glenoid fossa, one or more soft tissue structures, and combinations thereof.

In the disclosed methods, the determining of the desired location, inclination and version may further comprise;

determining a first point at an intersection of a scapula spine and a medial border of the scapula from the three-dimensional scan of the scapula;

determining a second point at the middle of a spinoglenoid notch from the three-dimensional scan of the scapula;

determining a first line through the first and second points;

determining a third point at a superior margin of the glenoid fossa from the three-dimensional scan of the scapula;

determining a forth point at an inferior margin of the glenoid fossa from the three-dimensional scan of the scapula:

determining a second line through the third and fourth points;

determining a desired inclination from an angle between the first and second lines.

In the disclosed methods, the determining of the desired location, inclination and version may further comprise:

determining a first point at an anterior margin of the glenoid fossa from the three-dimensional scan of the scapula;

determining a second point at a posterior margin of the glenoid fossa from the three-dimensional scan of the scapula.

determining a first line through the first and second points;
determining a third point at the midpoint of the glenoid fossa from the three-dimensional scan of the scapula;

determining a forth point at a vertebral border of the scapula from the three-dimensional scan of the scapula:

determining a second line through the third and fourth points;

determining a third line, which is perpendicular to the second line; and determining a desired version from an angle between the first and third lines.

A template used in a resurfacing procedure of a humeral head of a humerus is disclosed. One disclosed template comprises:

the template covering at least part of the humeral head and a patient specific anatomy disposed on a proximal humerus of the humerus, the template having a negative geometry that matches a positive geometry of the at least part of the humerus and the patient specific anatomy covered by the template;

the template comprising a guide for receiving a guide wire at a desired location, inclination and retroversion.

A cutting block for use with above-described template is disclosed. The disclosed cutting block comprises:

the cutting block mounted to the humeral head and comprising an upper cutting surface disposed at a desired resection angle, the block extending below the upper cutting surface and covering patient specific anatomy disposed on the proximal humerus;

the cutting block having a negative geometry that matches a positive geometry of the patient specific anatomy on the proximal humerus and a portion of the humeral head disposed between the patient specific anatomy on the proximal humerus and the upper cutting surface of the cutting block.

A template used in a resurfacing procedure of a glenoid fossa disposed on a scapula is disclosed. The disclosed template comprises:

the template covering at least part of the glenoid fossa and a patient specific anatomy disposed on the scapula, the template having a negative geometry that matches a positive geometry of the at least part of the glenoid fossa the and patient specific geometry of the scapula covered by the template;

The template comprising a guide for receiving a guide wire at a desired location, inclination and version.

Further areas of applicability of the invention will become apparent from the detailed description provided hereinafter. It should be understood that the detailed description and specific examples, while indicating the particular embodiment of the invention, are intended for purposes of illustration only and are not intended to limit the scope of the invention.

BRIEF DESCRIPTION OF THE DRAWINGS

The accompanying drawings, which are incorporated in and form a part of the specification, illustrate the embodiments of the invention and together with the written description serve to explain the principles, characteristics, and features of the invention. In the drawings:

FIG. 9 illustrates, a disclosed cutting block installed on the humeral head that is held in place by patient specific geometries derived from a 3D scan;

FIG. 10 is a top view of the cutting block illustrated in FIG. 9;

FIG. 11 is an illustration of another cutting block that makes use of patient specific geometries and that is provided with a hinge;

FIG. 12 is a two-part block with an upper portion connected to a cutting block via a dovetail connection wherein the upper portion is used as a guide to place the lower cutting block in place while the resection takes place along the anatomical neck of the humerus;

FIG. 13 is a partial sectional view of a cutting block apparatus used in a reverse shoulder implant procedure wherein the lower portion is anchored to the metaphyseal shaft and pins are used to hold the cutting block in place as the humeral head is resected at a 155° angle with respect to the transverse plane;

FIG. 14 illustrates an embodiment similar to that shown in FIG. 13 wherein the cutting block is equipped with an orientation pin that can adjust the cutting block with respect to the axis or the forearm;

FIGS. 15-16 illustrate the position of the patient while utilizing the apparatuses illustrated in FIGS. 13-14;

FIGS. 17-20 illustrate the installation of a cutting block utilizing patient specific geometry proximal to the anatomical neck of the humeral head for the purpose of providing a resection plane;

FIG. 21 illustrates yet another humeral head resection apparatus wherein a lower cutting block is connected distally of the greater tubercle and includes a proximal portion that stabilizes the cutting block based on proximal negative geometry of the humeral head and further provides a 155° angle between the resection plane and the transverse plane for a reverse implant procedure.

FIG. 22 is a top view of the apparatus of FIG. 21;

FIG. 23 illustrates yet another cutting block apparatus for a reverse implant procedure that is two-part with an upper or proximal portion connected to a lower or distal cutting block with a dovetail-type connection;

FIG. 24 is a top view of the cutting block and humeral template illustrated in FIG. 23.

FIGS. 35-36 illustrate the placement of a glenoid block and guide and the use of a posterior face of the glenoid as an anterior hard stop, the face of the glenoid as a medial hard stop, and a portion of the scapular neck as a superior hard stop;

FIGS. 37-38 illustrate a glenoid block and guide and the use of an anterior face of the glenoid as a posterior hard stop, the face of the glenoid as a medial hard stop and a portion of the scapular neck as a superior hard stop;

FIGS. 39-40 illustrate a glenoid block and guide and the use of the face of the glenoid as a medial hard stop and a portion of the scapular neck as an anterior-posterior hard stop and a superior hard stop;

FIGS. 41-42 illustrate a variation of the embodiment shown in FIGS. 39-40, wherein a glenoid block and guide are shown and the glenoid block uses of the face of the glenoid as a medial hard stop and a portion of the scapular neck as an anterior-posterior hard stop and superior hard stop;

FIGS. 43-44 illustrate a glenoid block and guide wherein an arm of the glenoid block uses of a junction of the coracoid and glenoid face as an anterior and inferior hard stop;

FIG. 49 is a sectional view of a scapula, glenoid base plate and locking screws that are the result of 3D images, surgeon review, engineers creating a virtual model of the patient's scapula, additional surgeon review and the creation of a best-fit 3D model created by both surgeons and engineers to avoid a locking screw extending through scapula cortical bone or a "breakout" situation;

FIG. 50 is an illustration of a glenoid block on a glenoid fossa;

FIG. 51 illustrates glenoid block of FIG. 50 after insertion of the guide wire guide or boss;

FIG. 52 is a bottom view of the scapular spine and glenoid block illustrated in FIG. 51;

FIG. 53 is an illustration of a guide wire inserted through the guide or boss of the glenoid block illustrated in FIGS. 55-52;

FIG. 54 illustrates the guide wire inserted into the glenoid fossa after removal of the guide or boss illustrated in FIG. 53;

FIG. 55 illustrates the guide wire extending out of the glenoid fossa after removal of the glenoid block shown in FIGS. 50-54;

FIGS. 56-57 illustrate the guide wire extending out of the glenoid fossa before (FIG. 56) and after reaming (FIG. 57);

FIG. 58 illustrates the installation of an inferior bone screw drill guide of a two-piece drill guide at the inferior end of a glenoid fossa;

FIG. 59 illustrates the coupling of superior bone screw drill guide to the inferior bone screw drill guide illustrated in FIG. 58 using a dovetail-type to T-slot coupling arrangement;

FIGS. 60-61 illustrate the coupling of drill guides to the superior bone screw drill guide shown in FIG. 59 for drilling peripheral screw holes;

FIG. 62 is a front plan view of the inferior bone screw drill guide and superior bone screw drill guide shown in FIGS. 58-61;

FIG. 63 illustrates the central hole drilled over the guide wire and use peripheral holes drilled through the superior bone screw drill guide prior to installation of the glenoid base plate;

FIGS. 64-66 illustrate the installation of the glenoid base plate and locking screws;

FIGS. 67-69 illustrate a successful installation of a glenoid base plate and locking screws using the techniques disclosed herein without breakout or without the screws passing through the cortical structure of the scapula;

FIGS. 70-71 are side views of the glenoid block 310 before and after reaming of the glenoid fossa;

FIG. 72 is a side view of a disclosed two-piece bone screw drill guide illustrating a need for medial-lateral degree of freedom provided by the disclosed two-piece bone screw drill guide.

DETAILED DESCRIPTION

The following description of the depicted embodiment(s) is merely exemplary in nature and is in no way intended to limit the invention, its application, or uses.

Humeral Head Resurfacing and Humeral Head Templates

Figure 1:
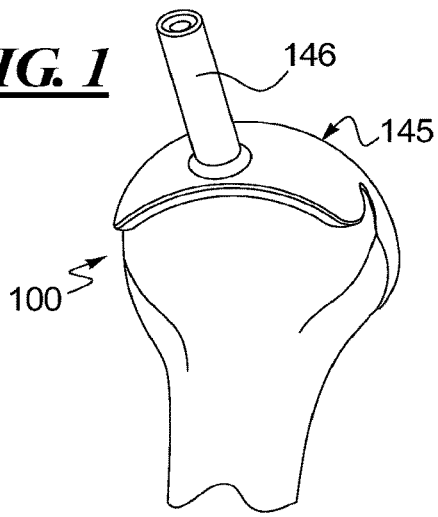
FIGS. 1-2 illustrate a humeral head template and guide fabricated using a 3D scan.
Figure 2:
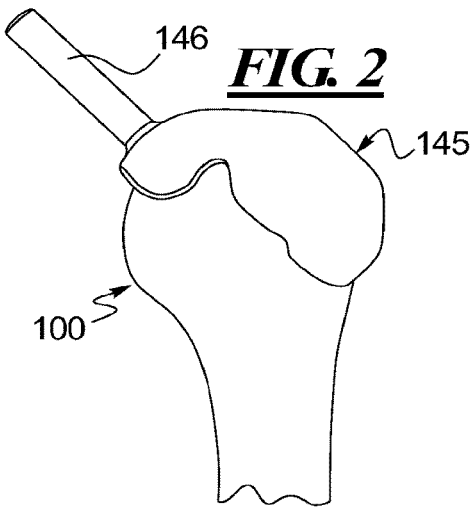

Disclosed methods and devices for resurfacing humeral heads are shown and described in FIGS. 1-12. Turning to FIGS. 1-2, the humeral head 100 is imaged using a computerized axial tomography (CAT or CT) scan or a magnetic resonance image (MRI) or other suitable 3D scanning method. The 3D scan is used to provide patient specific anatomy that can be used to generate a custom humeral head template 145 that may be equipped with a guide 146 for receiving a guide wire. The guide 146 and humeral head template 145 may be fabricated separately or as a unitary structure. The amount of patient-specific anatomy that can be used to stabilize the humeral head template 145 may be determined by the surgeon or may be standardized based upon future established procedures or by the manufacturer. Patient-specific anatomy that can be used to stabilize the humeral head template 145 in place may include, but is not limited to the following: an articular surface; a diseased area on an articular surface; a bicipital groove; a greater tuberosity; a lesser tuberosity; a footprint of the greater tuberosity; the metaphyseal axis; the anatomical neck of the humeral head 100; an anterior humeral head; a posterior humeral head; an anterior surgical neck; a posterior surgical neck; soft tissue structures; and combinations thereof.

Figure 3:
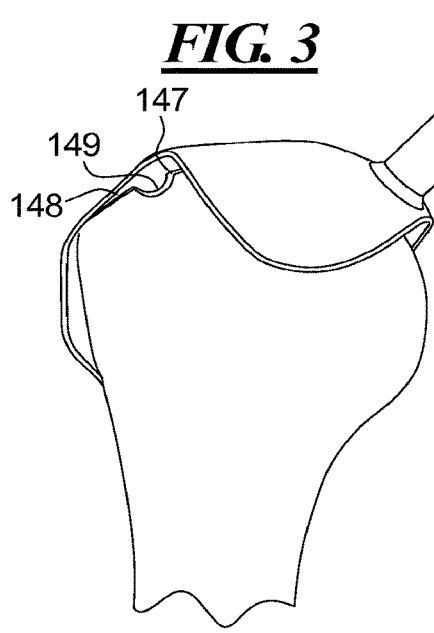
FIG. 3 illustrates the humeral head template of FIGS. 1-2 that provides clearance for soft tissue.
Figure 4:
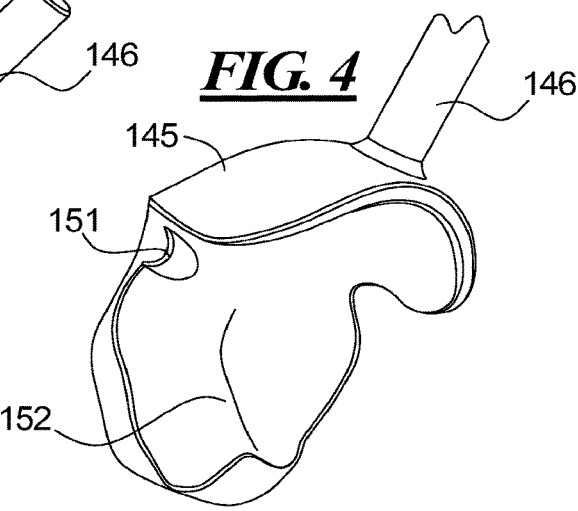
FIG. 4 illustrates the humeral head template of FIGS. 1-3 whereby the partial footprint of the greater tuberosity and the biceps groove are used to hold the template in place.
Figure 5:
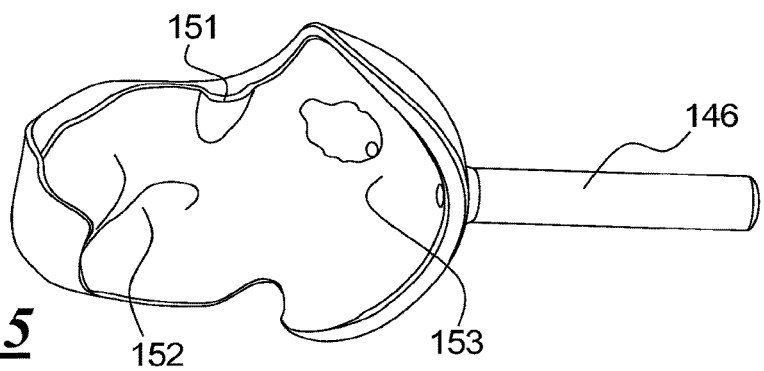
FIG. 5 is another view of the template of FIG. 4 further illustrating the use of a diseased area on an articular surface of the humeral head along with the biceps groove and partial footprint of the greater tuberosity to hold the template in place during insertion of the guide wire.

For example, the greater tuberosity 147 and lesser tuberosity 148 can be partially seen in FIG. 3. A portion of the bicipital groove 149 can also be seen in FIG. 3. Turning to FIG. 4, a partial footprint 151 of the greater tuberosity or greater tubercle is created in the customized humeral head template 145 as a ridge 152 that corresponds to the bicipital groove 149. Additional views of the footprint 151 and ridge 152 are provided in FIG. 5. In addition, FIG. 5 illustrates a pattern 153 that represents a negative geometry of a diseased area on an articular surface of the humeral head 100.

Figure 6:
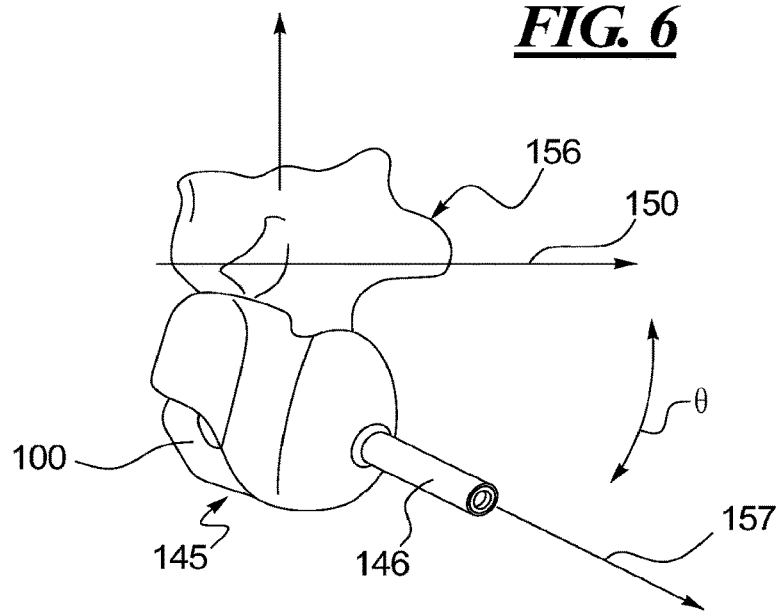
FIG. 6 is a top view of the humeral head template of FIGS. 1-5 illustrating patient specific retroversion from the transepicondylar axis of the distal humerus.
Figure 7:
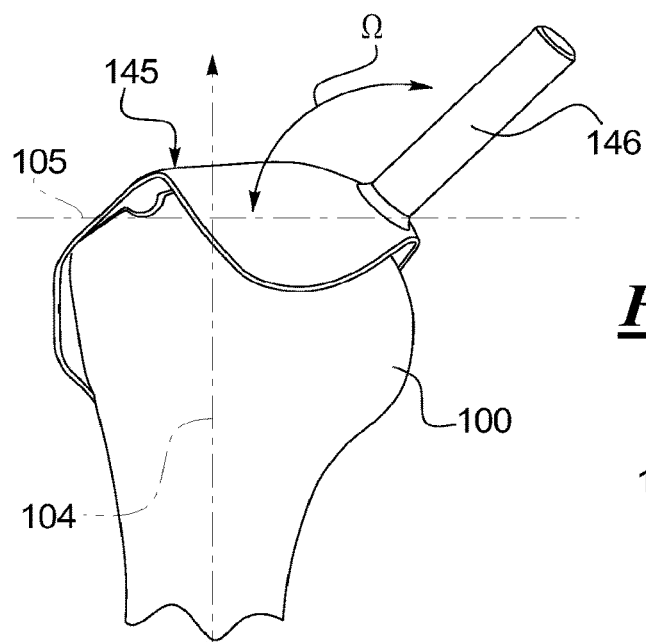
FIG. 7 is a plan view of the humeral head template of FIGS. 2-7 illustrating patient specific inclination derived from an axis perpendicular to the metaphyseal axis.
Figure 8:
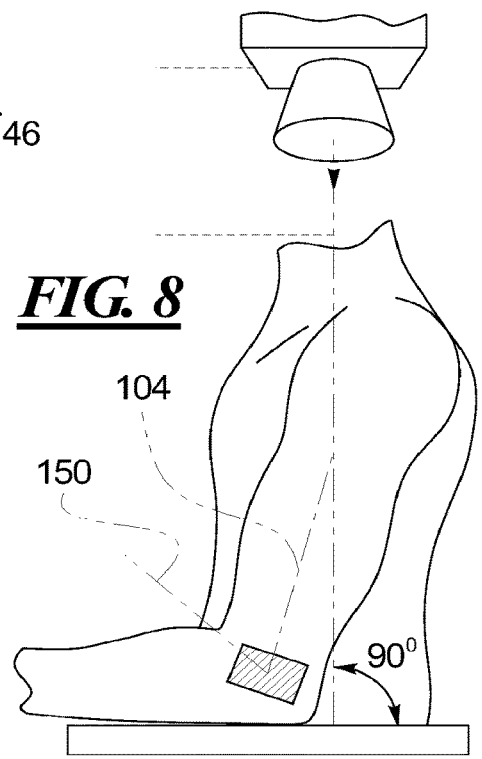
FIG. 8 is a schematic illustration of an x-ray taken from the superior side of the humeral head towards the transepicondylar axis at the elbow which has been marked.
Figures 25, 26:
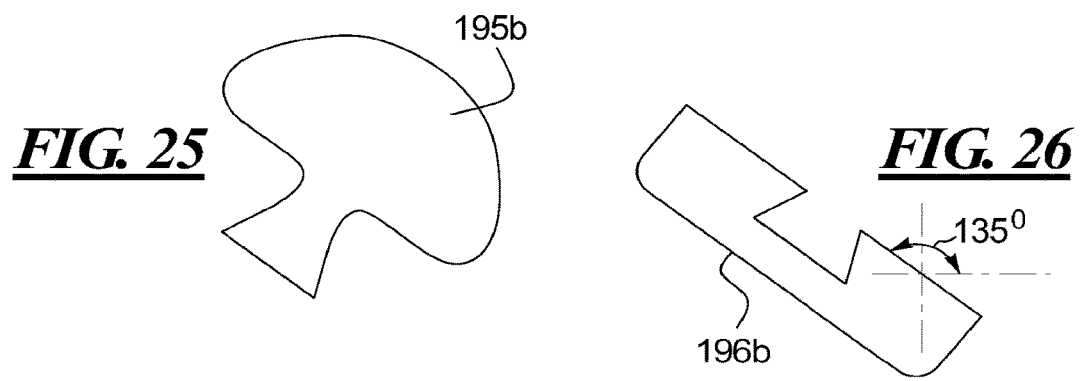
FIG. 25-27 illustrate a proximal humeral head template (FIG. 25) and two cutting blocks that may be connected to the humeral head template via a dovetail-type connection wherein the surgeon may not be able to assess the deficiency of the rotator cuff preoperatively and therefore the cutting block of FIG. 26 can be used for a standard shoulder implant procedure and the cutting block of FIG. 27 can be used for a reverse shoulder implant procedure.

Turning to FIGS. 6-7, the 3D scan of the proximal humerus or humeral head 100 can be used to insure that the guide wire is placed in the optima location in the center of the humeral head 100. An optimal guide wire location corresponds to an optimal implant fit. Thus, a desired inclination and retroversion can be determined in large part by patient-specific anatomy and discussed with the surgeon prior to fabricating the humeral head template 145. For example, the humeral head template 145 is designed with the patient-specific retroversion angle θ, which is determined by the transepicondylar axis 150 of the distal humerus 156 and a line 157 that bisects the humeral head 100. The guide wire will be inserted through the guide 146 along the line 157. The extent of the humeral torsion or retroversion typically ranges from about 20° to about 40°. A superior-inferior x-ray as illustrated in FIG. 8 can be used to determine the angle θ between the transepicondylar axis 150 and the coronal plane 104 for purposes of determining the retroversion preoperatively.

Turning to FIG. 7, the inclination Ω is the angle between the anatomical neck and the coronal plane 104. The inclination angle Ω can range from about 120° to about 150° as indicated in FIG. 7. The transverse plane is indicated at 105.

The humeral head template 145 and guide 146 are fabricated using currently available computer aided design (CAD) programs and finite element analysis (FEA) software based upon the data taken from the 3D scan of the humerus, which may be a CT, MRI, or other suitable scan. For example, once a profile is fixed in space in a 3D model of a humeral head 100, a humeral head template 145 may be created having a negative profile and superimposed on the 3D model of the humeral head 100. Available software may perform iterative test runs to predict whether small adjustments to the position of the humeral head template 145 are necessary to optimize performance. The fabrication of the humeral head template 145 may be performed before or after the humeral head 100 is reamed. It may be preferable to ream the humeral head 100 after the guide wire 106 is inserted through the guide 146.

One advantage to using a CT scan or MRI for only the humeral head 100 or proximal portion of the humerus is to limit the radiation exposure to the patient. By employing a combination of a 3D image and a standard x-ray as illustrated in FIG. 8, the radiation exposure to the patient is minimized. In short, the disclosed method uses a minimal amount of 3D scanning in conjunction with an axial x-ray to establish the desired retroversion.

After the guide wire 106 is inserted through the guide 146, the humeral head template 145 and guide 146 may be removed and the humeral head 100 reamed to a spherical shape for receiving an implant. As an alternative, 3D imaging in combination with CAD and FEA software may be employed to create patient-specific humeral cap implants produced to match the irregularly shaped humeral heads.

In any case, the methods described above enable the surgeon to determine retroversion and inclination preoperatively. The above methods and customized humeral head template 145 provides stability for the precise placement of the guide wire through the guide 146. As a result, optimal spherical implant 109 positioning on a non-spherical humeral head 100 can be achieved.

Humeral Head Resection and Patient Specific Cutting Blocks

For more severe cases, resection of the humeral head 100 is required. Various apparatuses or tools and techniques for resecting a humeral head 100 will be described below in connection with FIGS. 9-29. Turning first so FIG. 9, a 3D scan of a humeral head 100 has been taken and a cutting block 165 has been fabricated that exploits patient-specific geometries of the anterior, superior and inferior portions of the humeral head 100 that may include, but are not limited to tuberositites, osteophytes, the biceps groove, soft tissue insertion points, etc. The above geometry is typically located distally to the anatomical neck 166. The cutting block 165 could also be generated from any combination of anterior, posterior, inferior and superior anatomy. Only one cutting block 165 is required for a resection. Divergent or convergent pinholes 167 may be employed for receiving bone spikes, trocar pins, speed pins or bone screws to secure the cutting block 165 to the humeral head 100. An extended surface 168 provides a guide for the blade of the saw (not shown). Alternatively, the cutting block 165 may incorporate a slot for the saw blade. The patient-specific geometry, or more precisely, a negative of the patient-specific geometry, is disposed along the inside surface 169 of the cutting block 165.

In another embodiment shown in FIG. 11, a cutting block 171 is provided that includes two pieces 172, 173 that are hingedly connected together around the anatomical neck 166. Because the patient-specific anatomy alone should prevent the block 171 from slipping or moving, pinholes like those shown at 167 in FIG. 10 may not be needed although could be included, if desired. A negative patient-specific geometry of the anterior, superior and inferior portion of the humeral head may be included and may accommodate tuberositites, osteophytes, soft tissue insertion points, the bicep groove and other landmarks. The block 171 is particularly useful for patient-specific geometry located just distal to the anatomical neck 166. Screw lunges 175 may be employed as well as an extended surface like the one shown at 168 in FIG. 10. The embodiments of FIGS. 9-11 exploit patient-specific geometry located distally to the plane of the anatomical neck 166. Patient-specific geometry located proximally to the plane of the anatomical neck 166, such as the humeral head articular surface, may also be used alone or in combination with the above-referenced distal patient-specific geometry. For example, referring to FIG. 12, a dual piece block 177 includes a proximal piece 178 that partially covers the proximal humeral head and a lower cutting block piece 179 connected to the proximal piece 178 with a dovetail or T-slot type connection. A surface provides a guide for the blade of the saw. Alternatively, the cutting blocks 171, 177 may incorporate a slot for the saw blade.

For reverse shoulder implants, a cutting block 181 that exploits the flute of the metaphyseal shaft 183 may be employed that provides a fixed resection angle of 155°, or the angle between the cutting surface 184 and the transverse plane 105. The resection angle of 155° is standard for reverse shoulder implants. A surface provides a guide for the blade of the saw. Alternatively, the cutting block may incorporate a slot for the saw blade. A threaded orientation pin is shown at 185 and additional pins 186 may be used to secure the cutting block 181 to the humeral head 100. The threaded orientation pin 185 is also illustrated in FIG. 14, which allows the surgeon to confirm his/her orientation by aligning the pin with the forearm axis 187 as shown in FIG. 15. FIGS. 14-15 also illustrate the transepicondylar axis 150. The position of the patient during the resection procedure is illustrated in FIG. 16.

Another type of block 190 that relies upon patient specific anatomy generated from 3D scans just distal to the resection plane is illustrated in FIGS. 17-20. The block 190 utilizes pins or screws 191 and pinholes 192 to hold the block 190 in place during the resection procedure. The flat surface 193 serves as a convenient cutting guide. Alternatively, the cutting block 190 may incorporate a slot for the saw blade. One-piece or dual-piece block combinations can be utilized.

An additional one-piece cutting block 195 is illustrated in FIGS. 21-22, which includes a threaded orientation, pin 185 and additional stabilizing pins 186. A dual-piece configuration 195a is illustrated in FIGS. 23-24. The lower portions 196 include flat surfaces 197 that are used as cutting guides. Alternatively, the cutting block 195 may incorporate a slot for the saw blade.

Figure 27:
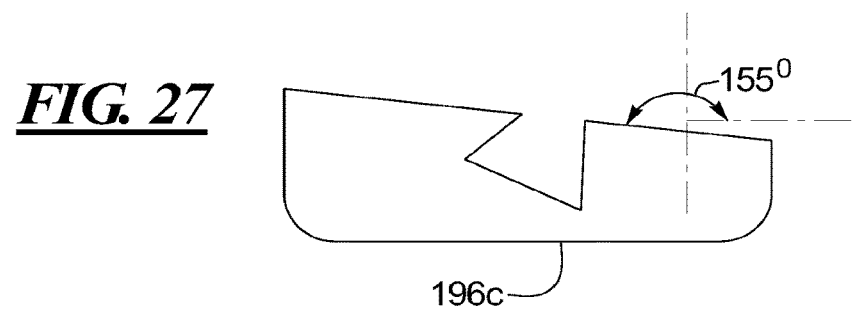

In certain cases, the surgeon may not be able to assess the deficiency of the rotator cuff until he or she has opened the patient and exposed the shoulder. In these situations, a decision as to whether to utilize a standard shoulder implant or a reverse shoulder implant may have been delayed. Because reverse shoulder implants include a 155° resection of the humerus, and a standard shoulder implant includes a lesser resection angle, e.g. 135°, a single upper portion 195b (FIG. 25) may be employed with two lower portions 196b (FIG. 26), 196c (FIG. 27). The lower portion 196b may be used for a standard shoulder implant and provides a resection angle of about 133°. The lower portion 196c may be used for a reverse shoulder implant and provides a resection angle of 155°. The upper portion 195b can be connected to the lower portions 196b or 196c using the dovetail-type connection shown in FIGS. 25-27 or a T-slot connection or similar connection means.

Figure 28:
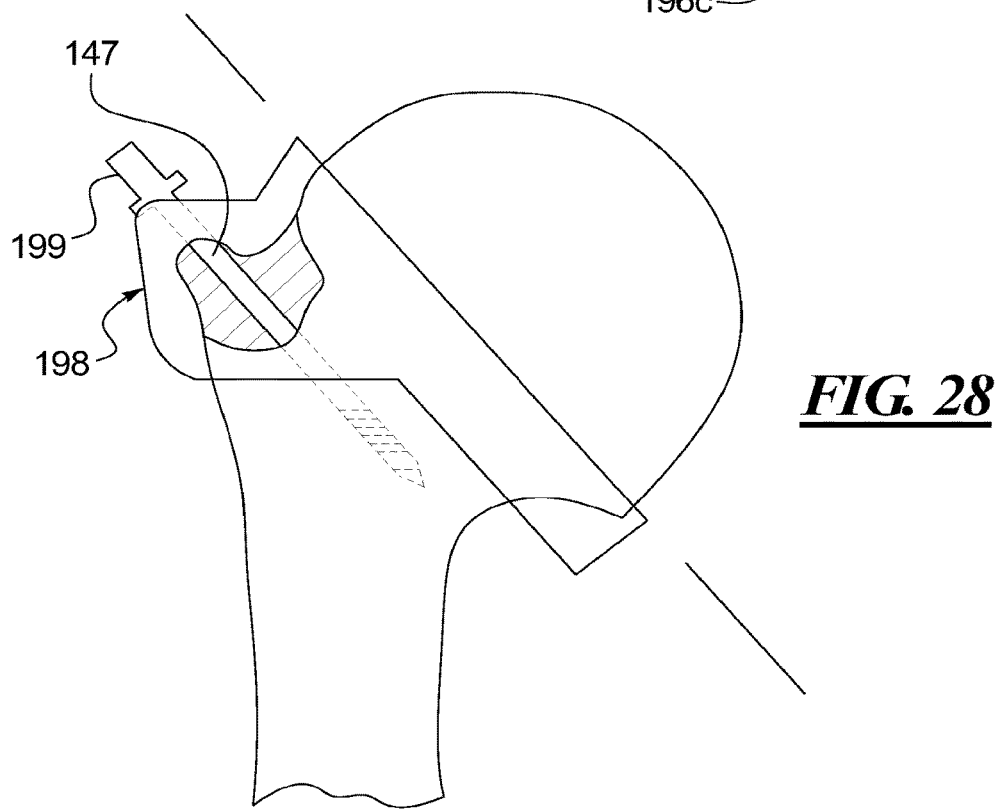
FIG. 28 illustrates a cutting block that is stabilized using lateral patient specific geometry.

Turning to FIG. 28, the cutting block 198 exploits lateral patient-specific negative geometry at the greater tuberosity 147 and is secured in place with a pin 199. A single pin 199 or multiple pins that are either convergent or divergent may be utilized. The amount of retroversion can be established using the procedure discussed below in connection with FIG. 8.

Figure 29:
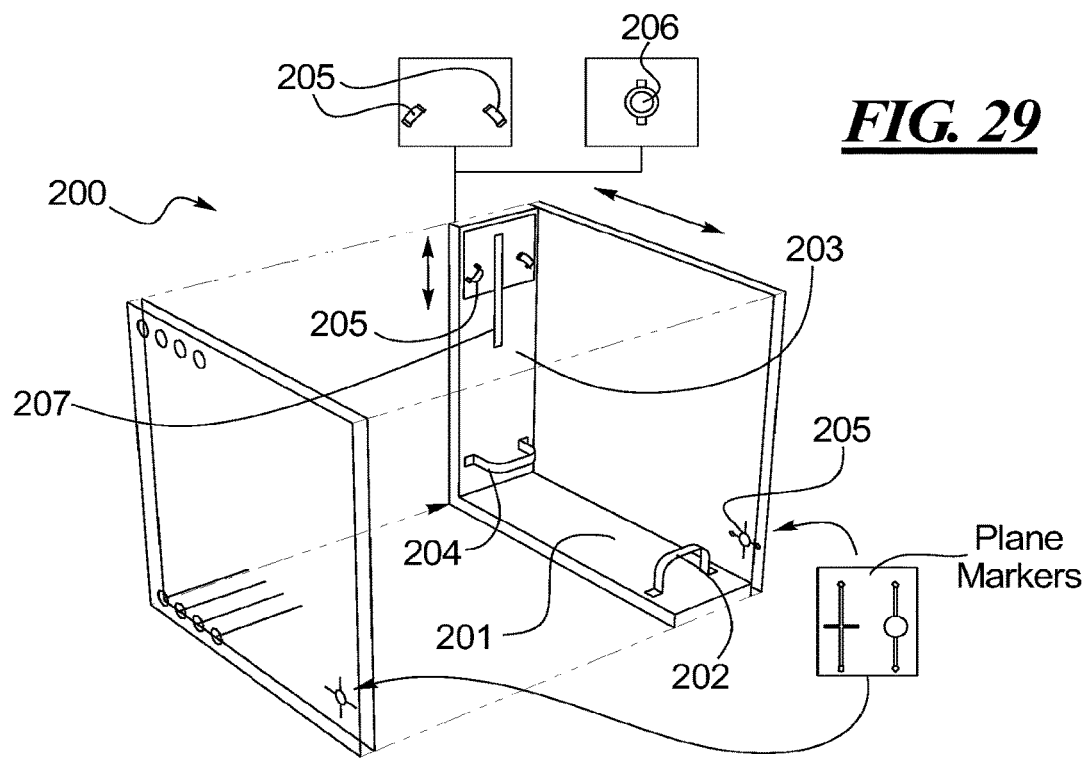
FIG. 29 schematically illustrates a jig for holding the patient's humerus, forearm and wrist in a proper position for carrying out the superior-inferior x-ray of FIG. 8.

In FIG. 29, a jig 200 is provided for the 3D scanning step and the axial x-ray step in order to insure that the humerus is parallel to the long axis of the scanner and to insure that the elbow is flexed at 90°. The jig 200 may aid in the determination of variables, such as version or inclination. Additionally, the jig may be used to consistently measure and compare anatomy. For example, anatomy could be measured and compared to predict usable instrumentation and/implants. The jig 200 is illustrated with a first plate 201 and strap 202 for holding the proximal humerus and a second plate 203 and straps 204, 205 for holding the elbow and hand/wrist or fingers respectively. If the patient is able to maintain his/her forearm in a vertical position, the vertical line 207 represents the forearm axis. The straps 202, 204, 205 can be fabricated from Velcro™, elastic, etc. A pistol or barrel grip 208 may be more comfortable and preferred by the patient. In some embodiments, the jig may include one or more markers that are visible by 3D scanning and/or x-ray.

Glenoid Fossa Resurfacing—Standard and Reverse Shoulder Implants

Figure 30:
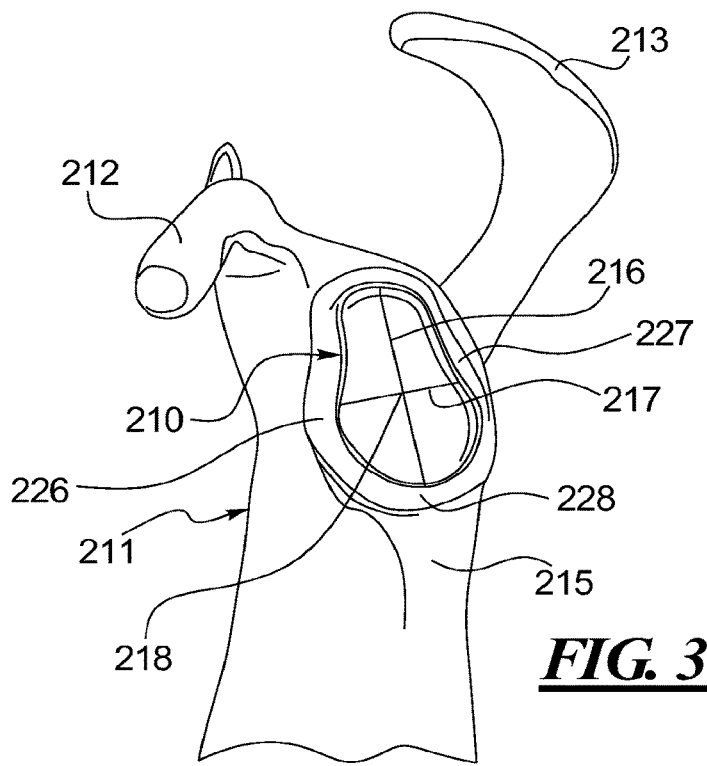
FIG. 30 illustrates a glenoid fossa that has been marked with the superior-inferior and anterior-posterior axes intersection for placement of a guide wire in a standard shoulder implant procedure.
Figure 31:
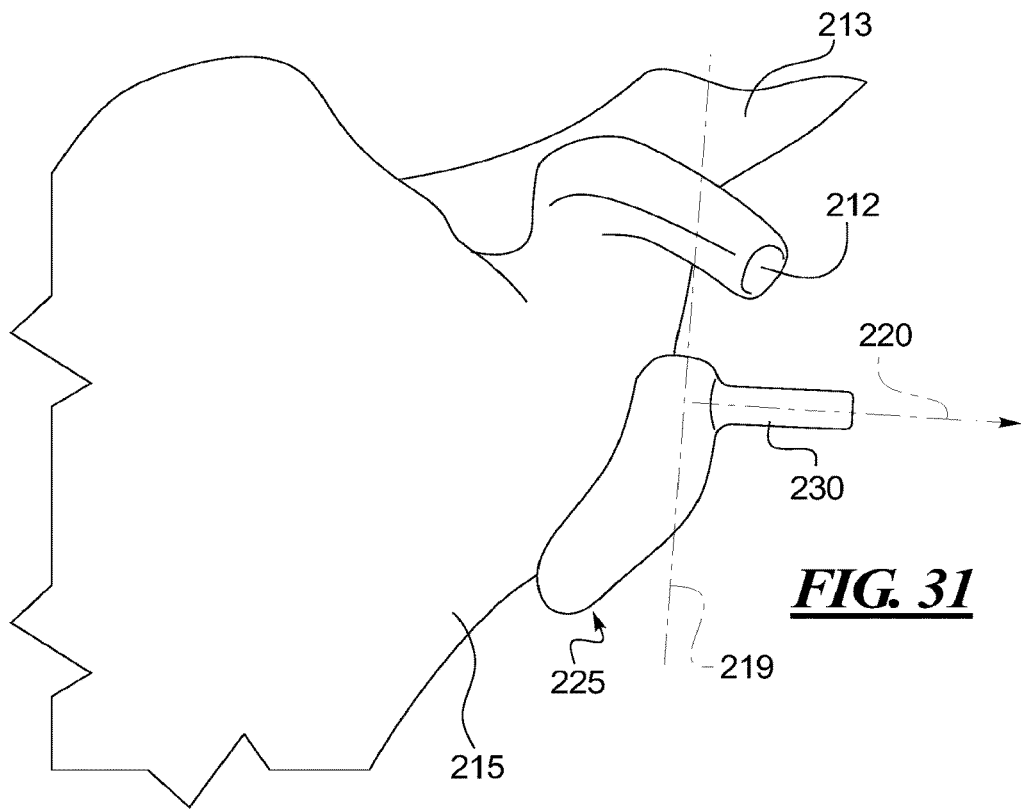
FIG. 31 illustrates the placement of a glenoid block and guide or boss for a guide wire on a glenoid illustrating the position of the guide at a 90° angle with respect to the plane of the original pre-disease glenoid face.

FIG. 30 illustrates a technique for choosing a template that provides optimal coverage of the glenoid fossa 210. The center of the template normally corresponds with the optical center or the glenoid fossa 210. In order to establish optimal insertion of the guide wire using the techniques disclosed herein, the intersection of a superior-inferior axis 216 and anterior-posterior axis 217 provides an optical center 218 which may provide an optimal insertion position for the guide wire during a standard shoulder implant procedure. For anatomical reconstruction, the glenoid fossa 210 should be reamed perpendicular to the original, non-diseased, face of the glenoid fossa 210. FIG. 31 illustrates the use of the 3D image to approximate the original plane 219 of the glenoid fossa 210. Returning to FIG. 30, various patient-specific anatomical features can be used for stabilizing a glenoid block 225 (FIG. 31) which will be used for insertion of a guide wire 106. Those patient-specific anatomical features include the coracoid 212, various features of the scapula 211 including the scapular spine 215 and portions of the acromion 213. Additional features for stabilizing a glenoid block 225 are also illustrated in FIG. 34, which include an anterior margin 226, a posterior margin 227, the lateral face 229 of the glenoid fossa 210 and the superior portion 228 of the scapular spine 215.

FIGS. 31-34 relate to glenoid blocks that may be used in both standard and reverse shoulder implant procedures. FIG. 31 illustrates the installation of a glenoid block 225 with a guide 230 that is perpendicular to the original plane 219 of the pre-diseased glenoid fossa 210. The coracoid and acromion are shown at 212, 213 respectively. The wide variety of patient-specific anatomical features that can be used to anchor or stabilize a glenoid block 225 will be illustrated in FIGS. 32-44 below.

Figure 32:
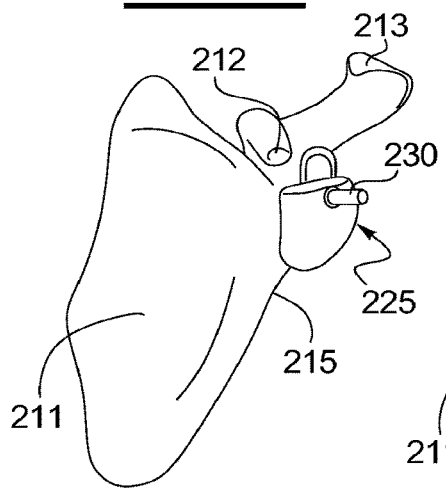
FIGS. 32-33 illustrate the use of patient specific geometry along inferior portions of the glenoid fossa and scapular neck for supporting the glenoid block of FIG. 31.
Figure 33:
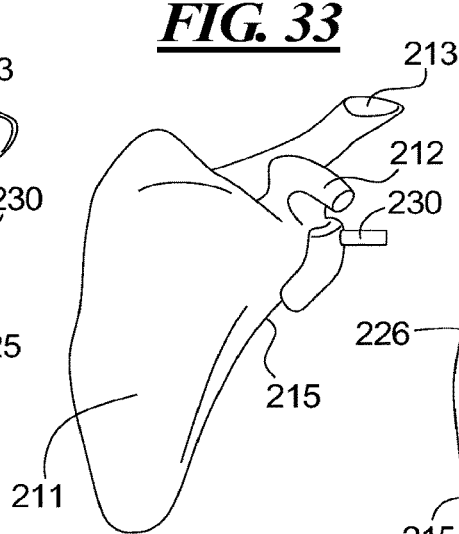
Figure 34:
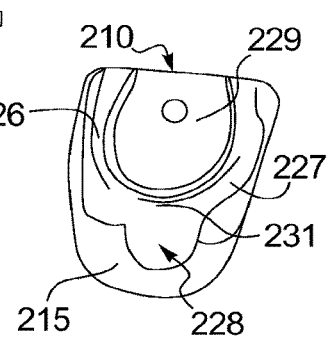
FIG. 34 illustrates various patient specific geometries that can be used to stabilize the glenoid block of FIGS. 31-33 including the glenoid face as a medial hard stop, anterior and posterior faces of the glenoid as posterior or anterior hard stops respectively and a portion of the scapular neck as a superior hard stop.

Turning to FIGS. 32-34, the superior portion 228 of the scapular spine 215 and inferior margin 234 of the glenoid fossa 210 are used to support the glenoid block 225. Because the glenoid block 225 illustrated in FIGS. 32 and 33 extends around the anterior and posterior side of the glenoid fossa 210, the anterior margin 226 and the posterior margin 227 (FIG. 34) provide posterior and anterior hard stops respectively. The superior portion 228 of the scapular spine 215 provides a superior hard stop. The lateral face of 229 of the glenoid fossa 210 provides a medial hard stop.

Turnings FIGS. 35-36, a glenoid block 235 engages the posterior side of the glenoid fossa 210 and a portion of the scapular spine 215. The slot 236 or narrow wall shown in FIG. 36 provides an anterior hard stop for she block 235. The surface 237 engages the lateral face of the glenoid fossa 210 and therefore provides a medial hard stop. The surface 238 (FIG. 36) that engages the scapular neck provides a superior hard stop.

Turning to FIGS. 37-38, the glenoid block 245 engages primarily the anterior side of the glenoid fossa 210 and therefore the slot or wall 236a (FIG. 38) provides a posterior hard stop, the face 237a provides a medial hard stop and the surface 338a provides a superior hard stop.

Turning to FIGS. 39-40, an additional glenoid block 255 is disclosed wherein portions of the block 255 engage inferior portions of the anterior and posterior sides of the glenoid fossa 210 as well as a superior portion of the scapular neck. Thus, turning to FIG. 40, the surface 237b provides a medial hard stop and the shaped slot or groove 238b provides an anterior, posterior and superior hard stop for the glenoid block 255.

A similar embodiment is illustrated in FIGS. 41-42 where the face 237c engages the face of the glenoid fossa 210 and provides a medial hard stop and the shaped slot 238c provides an anterior, posterior and superior hard stop.

A different technique is employed in FIGS. 43-44 wherein the glenoid block 275 includes an arm 276 that engages a junction of the coracoid and the glenoid fossa 210 to provide an anterior and posterior hard stop. The face 238d of the block 275 provides a medial hard stop.

Figure 45:
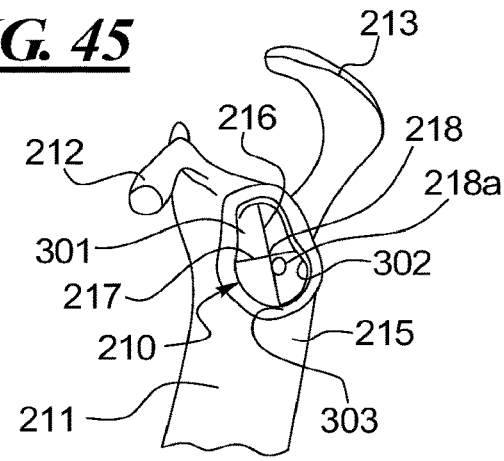
FIG. 45 is an illustration of a glenoid fossa marked with the intersection of a superior-inferior axis and a posterior-anterior axis and with an appropriate entry point for a guide wire in a posterior-inferior quadrant of the glenoid fossa for a reverse shoulder implant procedure.
Figure 46:
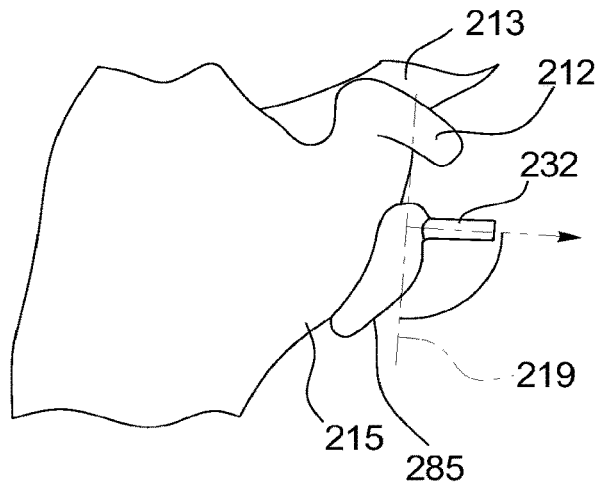
FIG. 46 illustrates a glenoid block and guide attached to a glenoid with a about 10° of inferior inclination provided by the guide for a reverse shoulder implant procedure.

Turning to reverse shoulder implant procedures and FIGS. 45-73, it is often recommended that the surgeon install the glenoid base plate in a slightly inferior and posterior position shown at 218a of FIG. 45. This placement of the guide wire and base plate is intended to minimize scapular notching. Therefore, the target 218a illustrated in FIG. 45 is disposed slightly below the anterior-posterior axis 217 and slightly posterior to the superior-inferior axis 216. Further, as shown in FIG. 46, it is sometimes optimal to apply a slight downward or inferior tilt to the guide wire and therefore FIG. 46 illustrates a non-perpendicular relationship between the guide 232 and the original plane 219 of the glenoid fossa 210.

Figure 47:
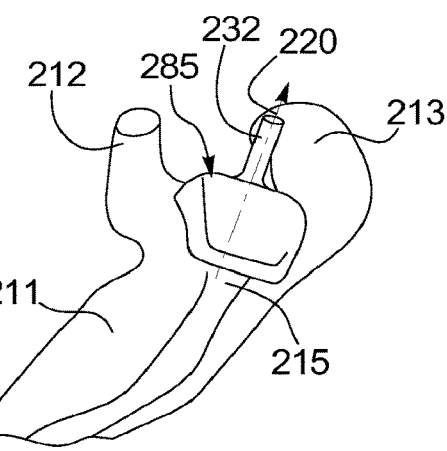
FIGS. 47-48 illustrate the placement of glenoid blocks with guides for use in a reverse shoulder implant procedure and the glenoid block of FIG. 48 illustrates the use of an additional reference hole for alignment purposes.
Figure 48:
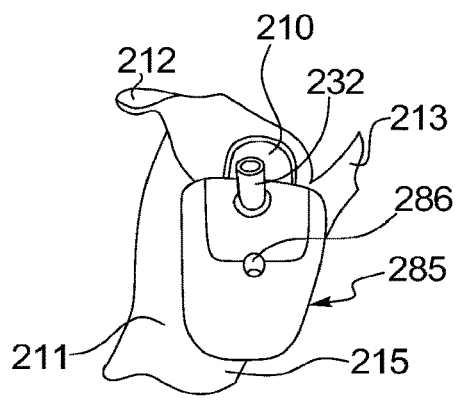

FIGS. 47-48 illustrate placement of the glenoid block 285 and guide 232 to a glenoid fossa 210 with about a 10° of inferior inclination provided by the guide 232. FIG. 48 also illustrates the use of an additional reference hole 286 for alignment purposes. The reference hole is intended to help prevent rotation of the glenoid base plate 285 during installation, which could cause one of the locking screws to extend through the cortical bone structure of the scapula 211.

The glenoid blocks 225, 235, 245, 255, 265, 275 and 285 illustrated in FIGS. 31-48 provide stable, inexpensive, disposable and patient-specific means for accurately placing a guide wire in a glenoid fossa 210 during both standard and reverse shoulder implant procedures. Preoperative determination of the optimal inclination and glenoid block version and possible use of a downward tilt on the guide wire are also possible so that fewer crucial decisions are made during surgery.

Glenoid Fossa Resurfacing for Reverse Shoulder Implants

FIG. 49 is a sectional view of a best-fit victual model created from 3D images, surgeon review and engineers creating the virtual model with additional input from the surgeon. The sectional image of FIG. 49 shows a scapula 211, glenoid base plate 136 and divergent locking screws 134, 135. The creation of the model illustrated in FIG. 49 is intended to avoid locking screws 134, 135, which should be long as possible for stability and strength, from extending through the cortical bone structure of the scapula 211, or in other words, creating a "breakout" situation. Methods and devices for creating the best-fit model illustrated in FIG. 49 are illustrated in FIGS. 50-73.

Turning to FIG. 50, a glenoid block 310 is installed over a glenoid fossa 210. A boss or guide 311 is inserted into the block 310 in preparation for insertion of a guide wire. A bottom view of the block 310 and guide 311, which are stabilized on the scapular spine 215 and in the posterior and anterior directions is shown in FIG. 52. FIG. 53 illustrates insertion of the guide wire 206 into the guide 311. FIG. 54 illustrates removal of the guide 311 and FIG. 55 illustrates removal of the glenoid block 310. FIGS. 56-57 illustrate the glenoid fossa 210 before reaming (FIG. 56) and after reaming (FIG. 57).

Two-Piece Drill Guides

FIG. 58 illustrates the central hole 138 that receives the central peg 137 of the glenoid base plate. The central hole 138 is created by rising a cannulated drill over the guide wire 206. FIGS. 58-59 also illustrate the installation of a two-piece bone screw drill guide 319 that includes a lower piece, referred to as the inferior bone screw drill guide 320 (FIG. 58) and an upper piece, referred to as the superior bone screw drill guide 322 that is slidably coupled to the inferior bone screw drill guide 320. The inferior bone screw drill guide 320 is installed on the infraglenoid tubercule and scapular spine 215 and includes a T-slot or dovetail-type connection for a slidable connection to a superior bone screw drill guide 322 as illustrated in FIG. 59. The T-slot or dovetail-type connection enables the superior bone screw drill guide to be adjusted laterally with respect to the face of the glenoid fossa 210. FIGS. 60-61 illustrate the coupling of drill guides 323 to the superior bone screw drill guide 322 for drilling divergent locking screw holes in the scapula 211. FIG. 62 illustrates the prepared screw holes 324, 325 through the superior bone screw drill guide 322 in preparation for receiving locking screws. FIG. 63 illustrates removal of the superior bone screw drill guide 322 and inferior bone screw drill guide 320 leaving the screw holes 324, 325 and central hole 138. FIG. 64 illustrates the installation of the glenoid base plate with the central peg 137 FIG. 101) inserted into the central hole 138. FIGS. 65-66 illustrate the installation of the locking screws 134, 135.

Turning to FIGS. 67-69, sectional views illustrate an optimal installation of a glenoid base plate 136 without either locking screw 134 or 135 entering the cortical bone structure of the scapula 211.

FIGS. 70-71 illustrate side views of the glenoid block or guide wire placement block 310 before and after reaming of the glenoid fossa 210 and the need for the medial-lateral degree of freedom provided by the two-piece bone screw drill guide 319. FIG. 72 further illustrates the advantage of the medial-lateral adjustability of the superior bone screw drill guide 322 with respect to the inferior bone screw drill guide 320 for more accurate placement of the holes used to anchor the locking screws 134, 135.

Figure 73:
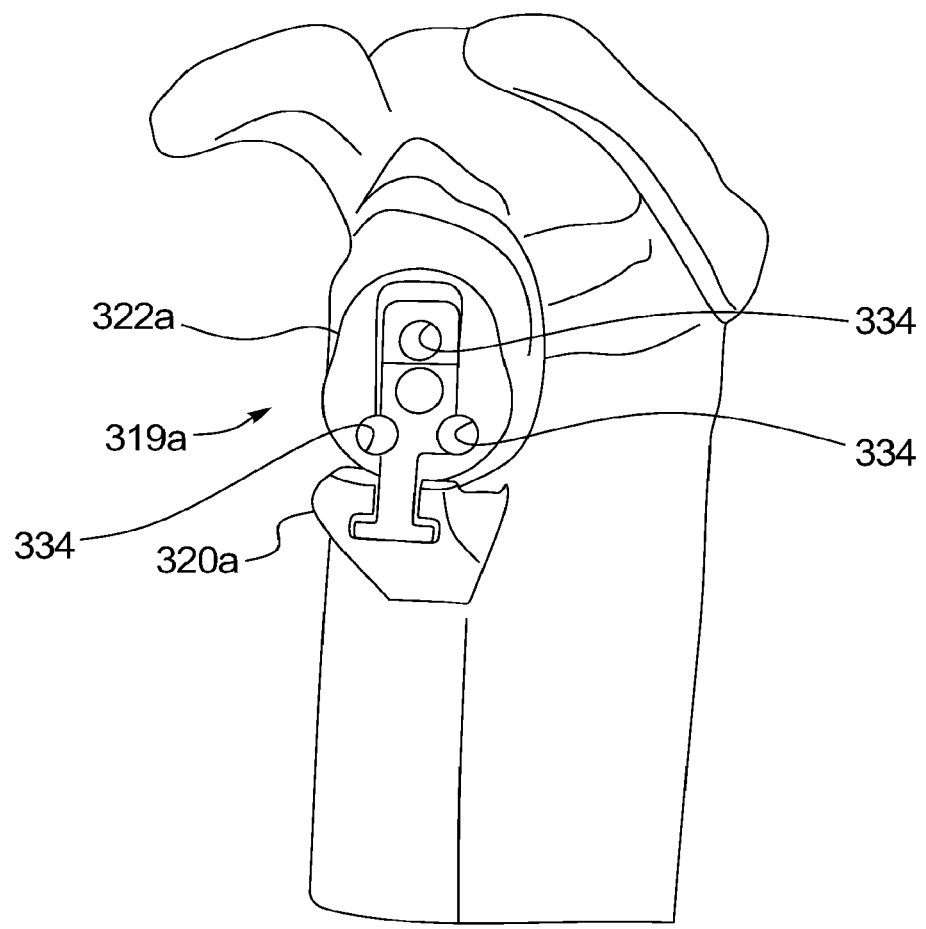
FIG. 73 is a front view of a two-piece drill guide that can be used in standard shoulder implant procedures where the glenoid implant includes a central peg and three peripheral pegs that are cemented to the glenoid fossa.

FIG. 73 illustrates a two-piece drill guide 319a that may be used for standard glenoid implants. Similar to the two-piece bone screw drill guide 319 used for reverse shoulder implant procedures, the inferior drill guide 320a for a standard implant is installed on the infraglenoid tubercule and scapular spine 215 and includes a T-slot or dovetail-type connection for a slidable connection to a superior drill guide 322a that includes peripheral drill holes 334 that match the pattern of the peripheral pegs.

Images like those shown in FIGS. 30-73 can be presented to a surgeon for review preoperative so that the surgeon may pay close attention to the resulting orientation and position of the glenoid base plate 136 or glenoid implant 136a and lengths of the locking screws 134, 135 if a reverse implant procedure is planned. After approving the models like those shown in FIGS. 30-73, the surgeon may then place an order and patient-specific instruments as shown in FIGS. 30-73 are fabricated prior to surgery.

In some cases, the surgeon may not be able to assess the deficiency of the rotator cuff until surgery has begun. In these cases, multiple glenoid blocks may be provided and multiple superior bone screw drill guides may be provided that would allow the surgeon to implant a glenoid base plate 136 or a glenoid implant 136a that may be cemented in place without the need for locking screws. The disclosed methods also eliminate many freehand placement and orientation procedure including freehand placement of the guide wire, orientation and placement of the drill guides. The disclosed methods also substantially reduce the possibility of drilling too deep or using locking screws that could extend through cortical bone structure in reverse implant procedures.

As various modifications could be made to the exemplary embodiments, as described above with reference to the corresponding illustrations, without departing from the scope of the invention, it is intended that all matter contained in the foregoing description and shown in the accompanying drawings shall be interpreted as illustrative rather than limiting. Thus, the breadth and scope of invention should not be limited by any of the above-described exemplary embodiments, but should be defined only in accordance with the claims and their equivalents.

What is claimed is:

1. A system for resurfacing a humeral head, comprising;
 a humeral head resurfacing template having a patient specific surface fabricated from an anatomical scan of a proximal humerus, the patient specific surface configured to at least partially achieve a stable engagement with an anatomical feature of the proximal humerus; and
 a cutting block having an upper cutting surface disposed at a desired resection angle, the cutting block extending below the upper cutting surface and configured to at least partially cover the anatomical feature of the proximal humerus;
 wherein the template has a negative geometry that matches a positive geometry of at least part of the proximal humerus and the anatomical feature; and
 wherein the cutting block has a negative geometry that matches a positive geometry of the anatomical feature of the proximal humerus and a portion of the humeral head disposed between the anatomical feature and the upper cutting surface of the cutting block.

2. The system of claim 1, further comprising a guide that receives a guide wire at a desired location, inclination and retroversion.

3. The system of claim 1, wherein the cutting block further comprises an extended surface for guiding a saw blade.

4. The system of claim 1, wherein the cutting block further comprises a slot for receiving a saw blade.

5. The system of claim 1, further comprising at least one pinhole for receiving a fastener to secure the cutting block to the humeral head.

6. A system for resurfacing a humeral head, comprising:
 a patient specific surface fabricated from an anatomical scan of a proximal humerus, the patient specific surface configured to at least partially achieve a stable engagement with an anatomical feature of the proximal humerus; and
 a guide that receives a guide wire at a desired location, inclination and retroversion,
 wherein the template includes a negative geometry that matches a positive geometry of at least part of the proximal humerus and the anatomical feature and a cutting block comprising:
 an upper cutting surface arranged at a desired resection angle, the cutting block extending below the upper cutting surface and configured to at least partially cover the anatomical feature of the proximal humerus; and
 wherein the cutting block has a negative geometry that matches a positive geometry of the anatomical feature of the proximal humerus, and wherein a portion of the humeral head is positioned between the anatomical feature and the upper cutting surface of the cutting block.

7. The system of claim 6, wherein the patient specific surface is configured to at least partially achieve a stable engagement with at least one of an articular surface, a bicipital groove, a greater tuberosity, a lesser tuberosity, a footprint of the greater tuberosity, a metaphyseal axis, an anatomical neck, and a soft tissue structure of the proximal humerus.

8. The system of claim 7, wherein the patient specific surface is configured to at least partially achieve a stable engagement with a diseased area on the articular surface of the proximal humerus.

9. The system of claim 7, wherein the patient specific surface is configured to at least partially achieve a stable engagement with an anterior surgical neck or a posterior surgical neck of the proximal humerus.

10. The system of claim 7, wherein the patient specific surface is configured to at least partially achieve a stable engagement with an anterior humeral head or a posterior humeral head of the proximal humerus.

11. The system of claim 7, wherein the patient specific surface is fabricated from a computer aided design (CAD) program and finite element analysis (FEA) software based on data obtained from the anatomical scan of the proximal humerus.

12. The system of claim 11, wherein the patient specific surface is fabricated from an image of the proximal humerus obtained from a computerized axial tomography scan or a magnetic resonance image.

* * * * *